(12) United States Patent
Mou et al.

(10) Patent No.: US 12,729,868 B2
(45) Date of Patent: Sep. 8, 2026

(54) INDOOR AIR CLEANING SYSTEM

(71) Applicant: Microjet Technology Co., Ltd., Hsinchu (TW)

(72) Inventors: Hao-Jan Mou, Hsinchu (TW); Chin-Chuan Wu, Hsinchu (TW); Chi-Feng Huang, Hsinchu (TW); Chieh-Yun Hsueh, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 339 days.

(21) Appl. No.: 18/406,408

(22) Filed: Jan. 8, 2024

(65) Prior Publication Data

US 2025/0198641 A1 Jun. 19, 2025

(30) Foreign Application Priority Data

Dec. 15, 2023 (TW) ................................ 112149109

(51) Int. Cl.
*F24F 3/167* (2021.01)
*A61L 9/014* (2006.01)
(Continued)

(52) U.S. Cl.
CPC ............... *F24F 11/58* (2018.01); *A61L 9/014* (2013.01); *A61L 9/20* (2013.01); *B01D 46/0028* (2013.01);
(Continued)

(58) Field of Classification Search
CPC .... F24F 11/58; F24F 3/16; F24F 8/108; F24F 8/22; F24F 11/77; F24F 11/89;
(Continued)

(56) References Cited

U.S. PATENT DOCUMENTS 5,997,619 A * 12/1999 Knuth ................ B01D 46/0038 55/385.2
2003/0040269 A1 2/2003 Yokoyama et al.
(Continued)

FOREIGN PATENT DOCUMENTS

CN 113932346 A 1/2022
CN 115342460 A 11/2022
(Continued)

OTHER PUBLICATIONS

Extended European Search Report for European Application No. 24153584.7, dated Jul. 18, 2024.

*Primary Examiner* — Frank M Lawrence, Jr.
(74) *Attorney, Agent, or Firm* — Birch, Stewart, Kolasch & Birch, LLP

(57) ABSTRACT

An indoor air cleaning system is disclosed and includes a gas detection module, an air cleaning device and a central control and regulation device. The gas detection module includes a microcontroller and a central control communication interface component for detecting and outputting air pollution data. The microcontroller processes the air pollution data and outputs a regulation signal based on the calculations. The air cleaning device includes a fan, a filtering element and a driving control component. The gas detection module is disposed inside the air cleaning device. The central control and regulation device is connected with the central control communication interface component under handshake communication protocol of wired communication or wireless communication to provide an control command to the gas detection module for activation operation of the fan. Consequently, the gas state in the indoor field is cleaned completely to meet the clean room requirement.

19 Claims, 13 Drawing Sheets

(51) Int. Cl.

| | |
|---|---|
| ***A61L 9/20*** | (2006.01) |
| ***B01D 46/00*** | (2022.01) |
| ***B01D 46/42*** | (2006.01) |
| ***B01D 46/44*** | (2006.01) |
| ***B01D 46/46*** | (2006.01) |
| ***F24F 3/16*** | (2021.01) |
| ***F24F 8/10*** | (2021.01) |
| ***F24F 8/108*** | (2021.01) |
| ***F24F 8/22*** | (2021.01) |
| ***F24F 11/58*** | (2018.01) |
| ***F24F 11/77*** | (2018.01) |
| ***F24F 11/89*** | (2018.01) |
| *F24F 110/10* | (2018.01) |
| *F24F 110/20* | (2018.01) |
| *F24F 110/64* | (2018.01) |
| *F24F 110/66* | (2018.01) |
| *F24F 110/70* | (2018.01) |
| *F24F 110/72* | (2018.01) |
| *F24F 110/74* | (2018.01) |

(52) U.S. Cl.

CPC ..... *B01D 46/0043* (2013.01); *B01D 46/4236* (2013.01); *B01D 46/429* (2013.01); *B01D 46/442* (2013.01); *B01D 46/448* (2013.01); *B01D 46/46* (2013.01); *F24F 3/16* (2013.01); *F24F 8/108* (2021.01); *F24F 8/22* (2021.01); *F24F 11/77* (2018.01); *F24F 11/89* (2018.01); *A61L 2209/111* (2013.01); *A61L 2209/12* (2013.01); *A61L 2209/15* (2013.01); *B01D 2273/30* (2013.01); *B01D 2279/51* (2013.01); *B01D 2279/65* (2013.01); *F24F 2110/10* (2018.01); *F24F 2110/20* (2018.01); *F24F 2110/64* (2018.01); *F24F 2110/66* (2018.01); *F24F 2110/70* (2018.01); *F24F 2110/72* (2018.01); *F24F 2110/74* (2018.01)

(58) Field of Classification Search

CPC ............... F24F 2110/10; F24F 2110/20; F24F 2110/64; F24F 2110/66; F24F 2110/70; F24F 2110/72; F24F 2110/74; F24F 3/167; F24F 11/39; F24F 11/56; F24F 8/10; F24F 2110/50; A61L 9/014; A61L 9/20; A61L 2209/111; A61L 2209/12; A61L 2209/15; B01D 46/0028; B01D 46/0043; B01D 46/4236; B01D 46/429; B01D 46/442; B01D 46/448; B01D 46/46; B01D 2273/30; B01D 2279/51; B01D 2279/65; Y02B 30/70

USPC ...... 95/1, 8, 10, 12, 14, 15, 19; 96/109–114, 96/224

See application file for complete search history.

(56) References Cited

U.S. PATENT DOCUMENTS

| | | | | |
|---|---|---|---|---|
| 2019/0234631 | A1* | 8/2019 | Wallace | B01L 1/04 |
| 2021/0339183 | A1* | 11/2021 | Hourani | B01D 39/2027 |
| 2022/0364748 | A1 | 11/2022 | Mou et al. | |
| 2023/0235914 | A1* | 7/2023 | Mou | F24F 11/88 454/239 |
| 2024/0263817 | A1 | 8/2024 | Sloof et al. | |

FOREIGN PATENT DOCUMENTS

| | | | |
|---|---|---|---|
| CN | 116510456 | A | 8/2023 |
| EP | 3 193 510 | A1 | 7/2017 |
| EP | 3 237 808 | B1 | 2/2020 |
| EP | 4 089 338 | A1 | 11/2022 |
| JP | 7-322370 | A | 12/1995 |
| JP | 2016-56996 | A | 4/2016 |
| JP | 2022-176062 | A | 11/2022 |
| JP | 2023-107714 | A | 8/2023 |
| JP | 2023-128402 | A | 9/2023 |
| JP | 2024-534360 | A | 9/2024 |
| TW | 201309980 | A1 | 3/2013 |
| TW | M607253 | U | 2/2021 |
| TW | 202225612 | A | 7/2022 |
| TW | 202244438 | A | 11/2022 |
| TW | 202331161 | A | 8/2023 |
| WO | WO 2016/038903 | A1 | 3/2016 |
| WO | WO 2020/255875 | A1 | 12/2020 |
| WO | WO 2023/041910 | A1 | 3/2023 |

* cited by examiner

| Class Code | Number of particles PM2.5 / $ft^3$ | Number of particles PM2.5 / $m^3$ |
|---|---|---|
| ZAPClean Room 1 | | 1 |
| ZAPClean Room 2 | | 10 |
| ZAPClean Room 3 | 3 | 100 |
| ZAPClean Room 4 | 28 | 1000 |
| ZAPClean Room 5 | 286 | 10000 |
| ZAPClean Room 6 | 2860 | 100000 |
| ZAPClean Room7 | 28600 | 1000000 |
| ZAPClean Room 8 | 77200 | 2720000 |
| ZAPClean Room 9 | 154300 | 5440000 |

FIG. 6

INDOOR AIR CLEANING SYSTEM

CROSS-REFERENCE TO RELATED APPLICATION

This application claims priority to Taiwan Patent Application No. 112149109, filed on Dec. 15, 2023. The entire contents of the above-mentioned patent application are incorporated herein by reference for all purposes.

FIELD OF THE INVENTION

The present disclosure relates to an indoor air cleaning system, and more particularly to an indoor air cleaning system having gas detection modules combined and electrically connected to each air cleaning device for implementing air pollution detection and coordinating the regulation operations.

BACKGROUND OF THE INVENTION

Suspended particles are defined as the solid particles or droplets contained in the air. Due to their extremely fine size, the suspended particles may enter the lungs of human body through the nasal hair in the nasal cavity easily, causing inflammation in the lungs, asthma or cardiovascular disease. If other pollutant compounds are attached to the suspended particles, it will further increase the harm to the respiratory system. In recent years, the issue of air pollution has been increasingly severe, especially with consistently high concentrations of suspended particles (e.g., PM2.5). Therefore, the monitoring to the concentration of the gas suspended particles is taken more and more seriously. However, the gas flows unstably due to the variable wind direction and the air volume, and the general gas-quality monitoring station is located in a fixed place. Under this circumstance, it is impossible for people to check the concentration of suspended particles in current environment.

Furthermore, in recent years, modern people are placing increasing importance on the quality of the air in their surroundings. For example, carbon monoxide, carbon dioxide, volatile organic compounds (VOC), PM2.5, nitric oxide, sulfur monoxide and even the suspended particles contained in the air are exposed in the environment to affect the human health, and even endanger the life seriously. Therefore, the quality of environmental air has attracted the attention of various countries. At present, how to detect the air quality and avoid the harm is a crucial issue that urgently needs to be solved.

In order to confirm the quality of the air, it is feasible to use a gas sensor to detect the air surrounding in the environment. If the detection information can be provided in real time to warn the people in the environment, it is helpful of avoiding the harm and facilitates the people to escape the hazard immediately, preventing the hazardous gas exposed in the environment from affecting the human health and causing the harm. Therefore, it is considered a valuable application to use a gas sensor detecting the air in the surrounding environment.

In addition, it is difficult to have the surveillance and control the indoor air quality. Besides the outdoor air quality, the indoor air-conditioning conditions and the pollution sources are the major factors affecting the indoor air quality. It is necessary to intelligently and quickly detect indoor air pollution sources in various indoor fields, effectively remove the indoor air pollution to form a clean and safe breathing gas state, and monitor indoor air quality in real time anytime, anywhere. Certainly, if the concentration of the suspended particles in the indoor space field is strictly controlled according to the "clean room" standard, it allows to avoid the introduction, generation and retention of suspended particles, and the temperature and humidity in the indoor space field are controlled within the required range. That is to say, the number of suspended particles in the air pollution of the indoor space field is used to distinguish their classifications, so that it allows the indoor space field to meet the clean room requirements for safe breathing.

At present, the air pollution detection of the indoor air purification system is implemented by the gas detector to transmit the air pollution information, and then the air pollution information is transmitted to the cloud computing service device through the Internet of Things communication, so that the air pollution information of the outdoor field and the indoor field is stored to form a big data database of air pollution data. Based on the intelligent calculation and comparison of the big data database of air pollution data, a control command is intelligently selected to be sent to the fan of the circulating filtering device to start the regulation operation. In that, an internal circulation directed airflow is continuously generated in the indoor field, and the air pollution is directed multiple times through the filtering element to be filtered and removed, so that the gas state in the indoor field has suspended particles meeting a specific specification quantity to reach a cleanliness of clean room.

In addition, the indoor air cleaning system includes multiple indoor cleaning devices and regulation devices arranged in the indoor field to regulate coordinately to achieve real-time monitoring of indoor air quality and real-time processing, filtering and cleaning. It makes the indoor air pollution completely clean and a clean and safe breathing gas state is formed. Therefore, how to regulate the above-mentioned cleaning devices in conjunction with the gas detection module is the main subject of the present disclosure.

SUMMARY OF THE INVENTION

One object of the present disclosure is to provide an indoor air cleaning system including a plurality of gas detection modules, a plurality of air cleaning devices and at least one central control and regulation device. Each air cleaning device is combined and electrically connected with a gas detection module disposed thereon for implementing air pollution detection and coordinating the regulation operations. Moreover, the central control and regulation device is connected with the gas detection module, and able to select an activation mechanism under the handshake communication protocol of wired communication or wireless communication for transmitting and connecting, so that control instruction signals are provided for the gas detection modules regulating the activation operations, the air volume and the noise of the plurality of air cleaning devices. It allows the air pollution to pass through the filtering elements of the air cleaning devices for filtration, so that the gas state in the indoor field is cleaned completely to meet the clean room requirements for safe breathing, and an indoor air cleaning system is achieved.

In accordance with an aspect of the present disclosure, an indoor air cleaning system is provided, and the system includes a plurality of gas detection modules, a plurality of air cleaning devices, and at least one central control and regulation device. The gas detection module includes a power conversion component, a sensing component, a microcontroller, a wireless communication component and a central control communication interface component. The power conversion component inputs an AC power to be converted into a required DC power outputted for the sensing component, the microcontroller, the wireless communication component and the central control communication interface component, the sensing component detects air pollution and outputs air pollution data for the microcontroller calculating and processing, the microcontroller outputs a plurality of regulation signals, and the sensing component includes a sensing element detecting the air pollution. The plurality of air cleaning devices are disposed in an indoor field, and each air cleaning device includes a fan, a filtering element and a driving control component, wherein the plurality of gas detection modules are disposed within the plurality of air cleaning devices, and electrically connected to the fan and the driving control component. The driving control component regulates an activation operation, airflow volume and noise of the fan according to the plurality of regulation signals received, so that the fan is controlled to start guiding the air pollution passing through the filtering element for filtration. The central control and regulation device is connected with the central control communication interface components of the plurality of gas detection modules under handshake communication protocol of wired communication or wireless communication to provide a control instruction signal to the gas detection module for regulating operations of the plurality of air cleaning devices, and receives the air pollution data detected by the gas detection modules for displaying in real time. Accordingly, the plurality of gas detection modules receive a control command and transmit the control command to the driving control components to regulate the activation operations of fans, whereby the fan is controlled to start guiding the air pollution passing through the filtering element for filtration, thereby the gas state in the indoor field is cleaned completely to meet a clean room requirement.

BRIEF DESCRIPTION OF THE DRAWINGS

The above contents of the present disclosure will become more readily apparent to those ordinarily skilled in the art after reviewing the following detailed description and accompanying drawings, in which:

FIG. 6 is a schematic diagram showing the classifications of the clean rooms for classifying the gas state in the indoor field of the present disclosure by counting the suspended particles with the particle size less than 2.5 μm.

DETAILED DESCRIPTION OF THE PREFERRED EMBODIMENT

The present disclosure will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 1A:
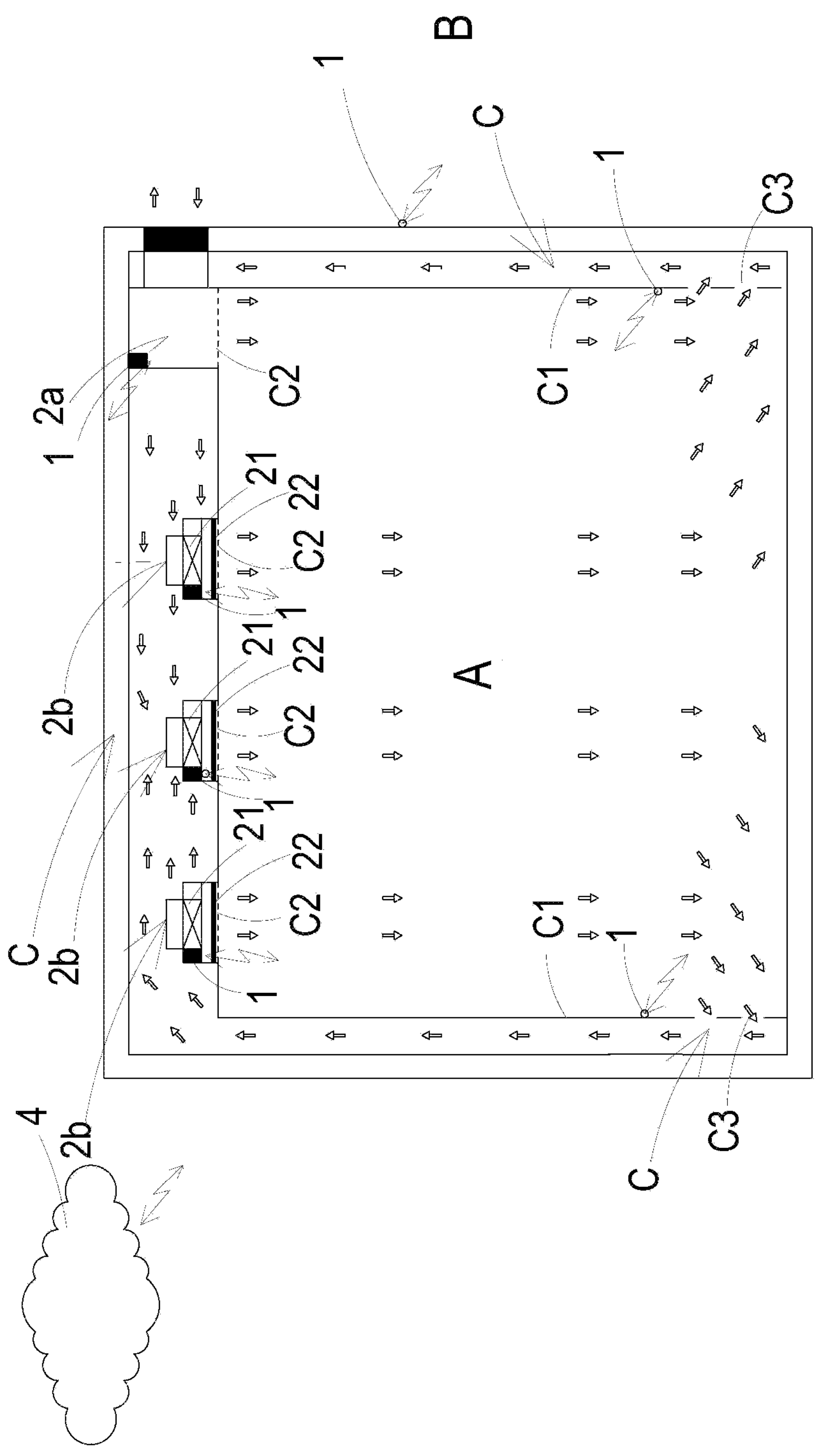
FIG. 1A is a schematic view illustrating an indoor air cleaning system implemented in an indoor field according to an embodiment of the present disclosure.
Figure 1B:
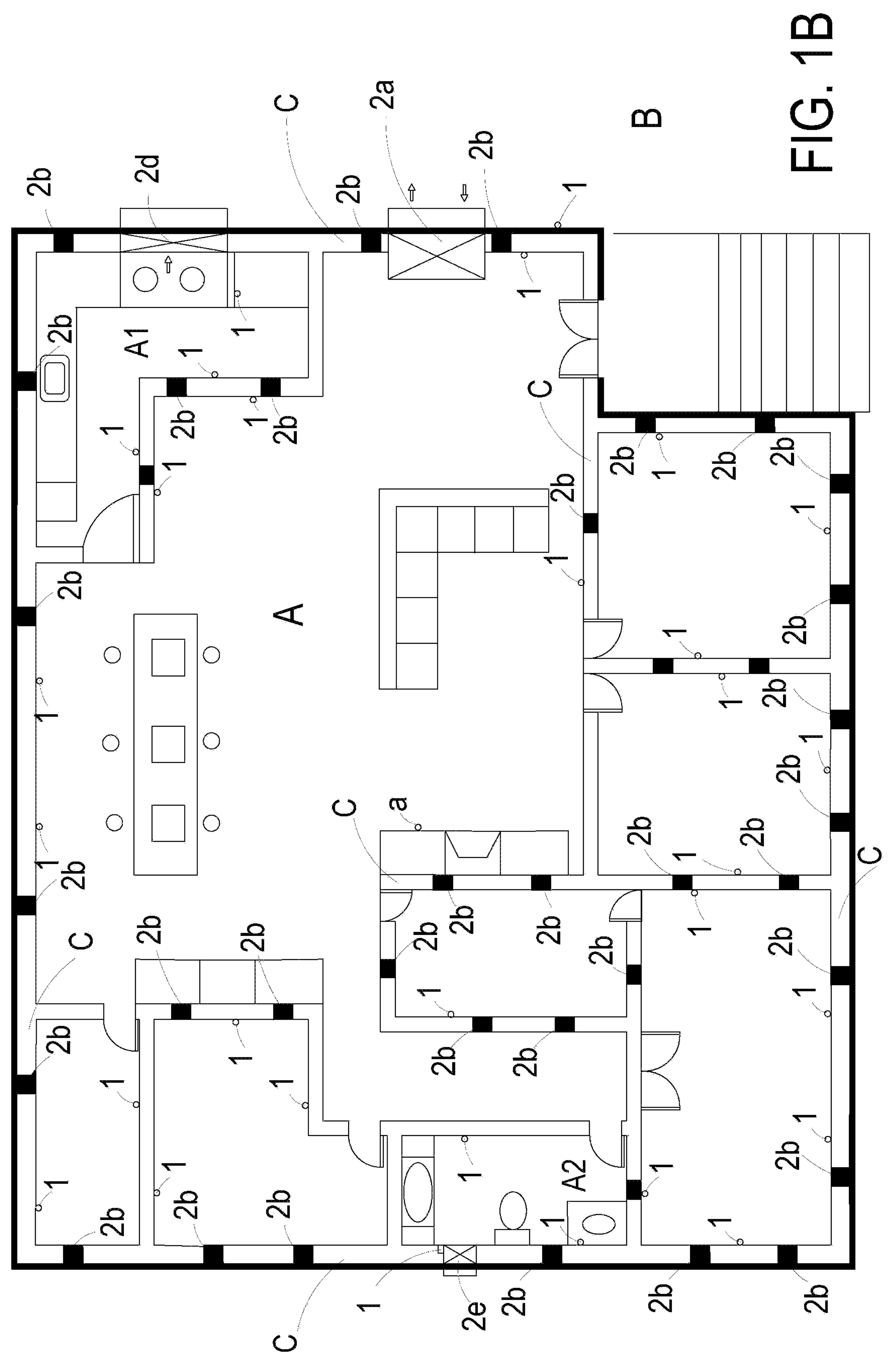
FIG. 1B is a schematic view illustrating an indoor air cleaning system implemented in an indoor field according to another embodiment of the present disclosure.
Figure 1C:
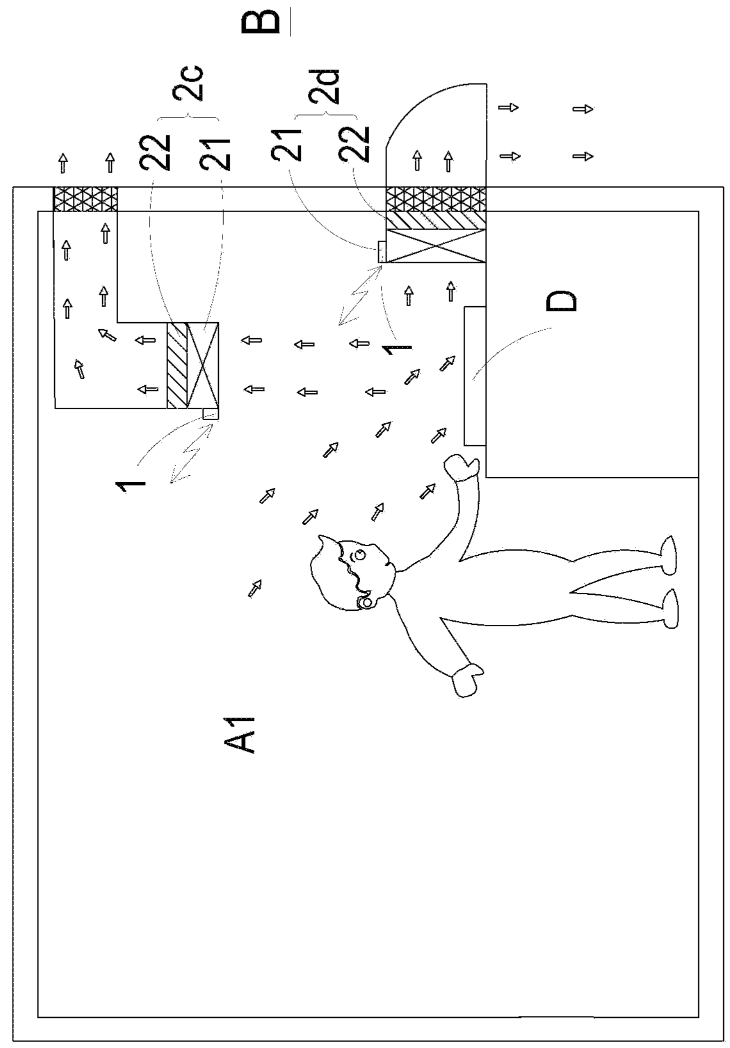
FIG. 1C is a schematic view illustrating an indoor air cleaning system implemented in a kitchen unit of an indoor field according to an embodiment of the present disclosure.
Figure 1C:
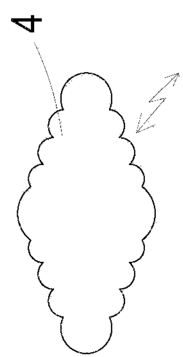

Please refer to FIG. 1A, FIG. 1B and FIG. 1C. The figures mentioned above illustrate an indoor air cleaning system of the present disclosure used in an indoor field A. The present invention provides an indoor air cleaning system, which mainly includes a plurality of gas detection modules 1, a plurality of air cleaning devices 2, a central control and regulation device 3 and a cloud computing service device 4.

Figure 2A:
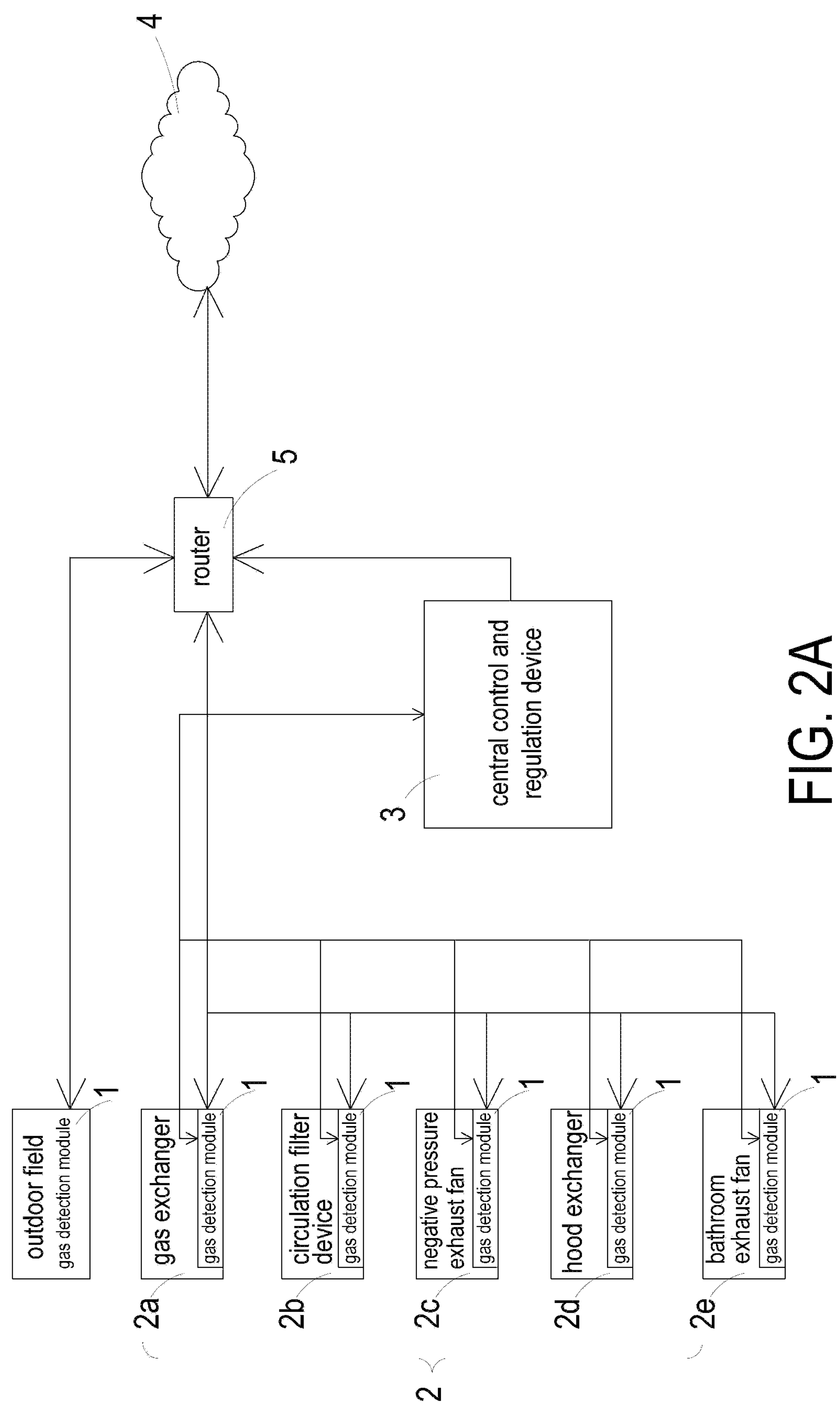
FIG. 2A is a schematic diagram illustrating a transmission relationship between the gas detection modules of the indoor air cleaning system of the present disclosure through wired communication or wireless communication.
Figure 2B:
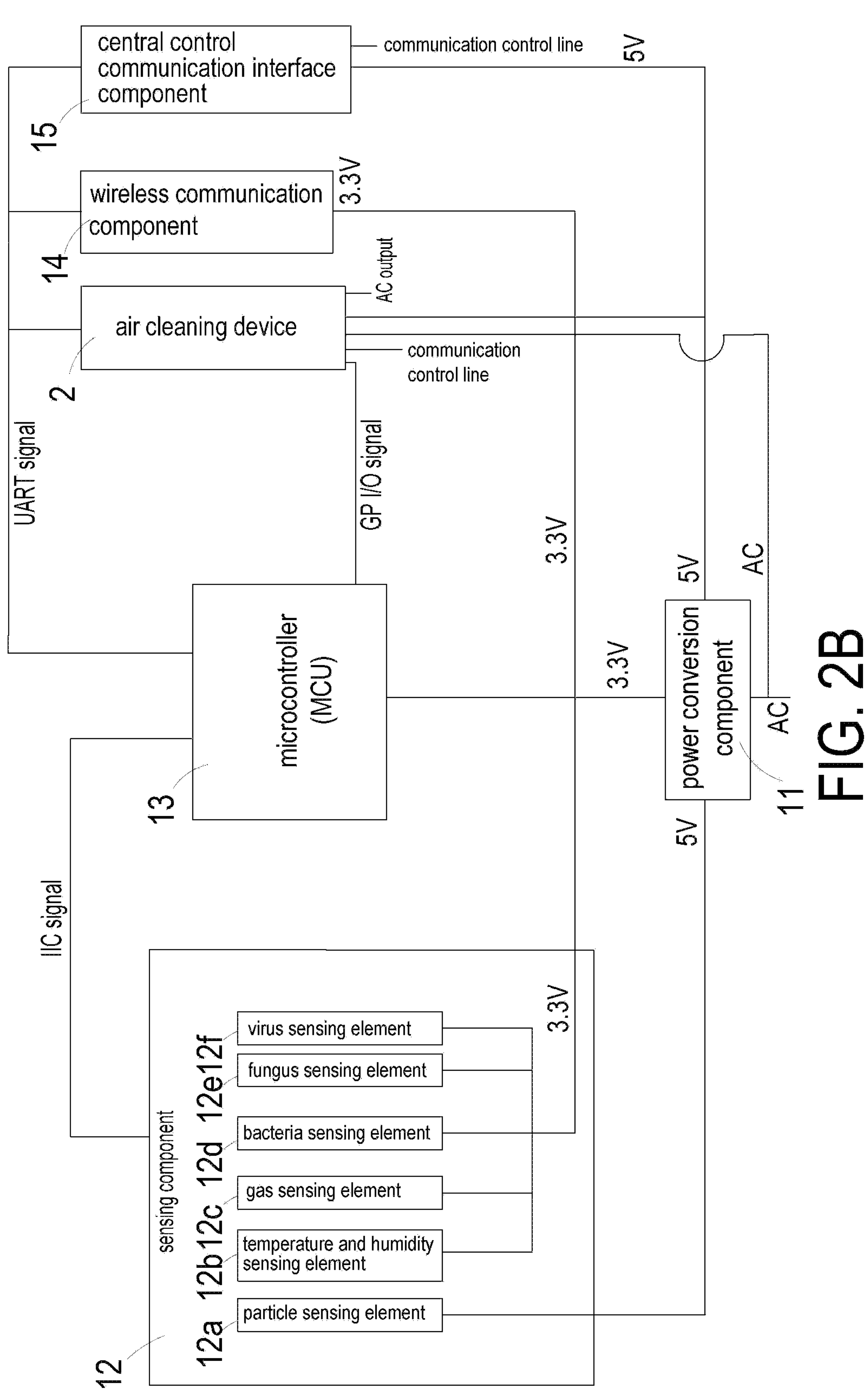
FIG. 2B is a schematic diagram illustrating a regulation-device control circuit of the gas detection module in the indoor air cleaning system according to an embodiment of the present disclosure.

Please refer to FIG. 2B. In the embodiment, the gas detection module 1 includes at least one power conversion component 11, at least one sensing component 12, at least one microcontroller (MCU) 13, at least one wireless communication component (WI-FI) 14 and at least one central control communication interface component 15.

In the embodiment, an AC power is inputted into the power conversion component 11 and converted as a required DC power, the DC power is then outputted for the sensing component 12, the microcontroller 13, the wireless communication component 14 and the central control communication interface component 15. Preferably but not exclusively, an AC power is inputted into the power conversion component 11 and converted into a required DC voltage of 5 V and a required DC voltage of 3.3 V, respectively. The required DC voltage of 5 V is provided to the sensing component 12, the microcontroller 13 and the central control communication interface component 15, and the required voltage of 3.3 V is provided to the sensing component 12 and the wireless communication component 14, but the present disclosure is not limited thereto.

In the embodiment, the sensing component 12 includes a sensing element for detecting air pollution. Preferably but not exclusively, the sensing component 12 is disposed in an indoor field A or an outdoor field B for detecting the air pollution, and outputs air pollution data for the microcontroller 13 calculating and processing. The microcontroller 13 outputs a plurality of regulation signals. Notably, in the embodiment, the air pollution is at least one selected from the group consisting of suspended particles, particulate matter, ozone, carbon monoxide, carbon dioxide, sulfur dioxide, nitrogen dioxide, acetaldehyde, acetamide, acetonitrile, acetophenone, 2-acetylaminofluorene, acrolein, acrylamide, acrylic acid, acrylonitrile, propylene chloride, 4-aminobiphenyl, aniline, o-anisidine, asbestos, benzene, benzidine, trichlorotoluene, benzyl chloride, biphenyl, di(2-ethylhexyl) phthalate (DEHP), dichloromethyl ether, tribromoform, 1-bromopropane, 1,3-butadiene, calcium cyanamide, caprolactam, captan, carbaryl, carbon disulfide, carbon tetrachloride, carbonyl sulfide, catechol, chloramben, chlordane, chlorine, chloroacetic acid, 2-chloroacetophenone, chlorobenzene, chlorobenzilate, chloroform, chloromethyl methyl ether, chloroprene, cresol/methanesulfonic acid (isomers and mixtures), o-cresol, m-cresol, p-cresol, cumene, 2,4-dichlorophenoxyacetic acid, salts and esters, dichlorodiphenyldichloroethylene (DDE), diazomethane, dibenzofuran, 1,2-dibromo-3-chloropropane, dibutyl phthalate, 1,4-dichlorobenzene, 3,3-dichlorobenzidine, dichloroethyl ether (bis(2-chloroethyl)ether), 1,3-dichloropropene, dichlorvos, diethanolamine, N,N-dimethylaniline, diethyl sulfate, 3,3-dimethoxybenzidine, dimethylaminoazobenzene, 3,3'-dimethylbenzidine, dimethylcarbamate chloride, dimethylformamide, 1,1-dimethylhydrazine, dimethyl phthalate, dimethyl sulfate, 4,6-dinitro-o-cresol and its salts, 2,4-dinitrophenol, 2,4-dinitrotoluene, 1,4-dioxane (1,4-ethylene dioxide), 1,2-diphenylhydrazine, epichlorohydrin (1-chloro-2,3-epoxy propane), 1,2-butylene oxide, ethyl acrylate, ethylbenzene, ethyl urethane (ethyl carbamate), ethyl chloride, dibromoethane, dichloroethane (1,2-dichloro ethane), ethylene glycol, ethyleneimine (azirine), ethylene oxide, ethylene thiourea, dichloroethane (1,1-dichloroethane), formaldehyde, heptachlor, hexachlorobenzene, hexachlorobutadiene, hexachlorocyclopentadiene, hexachloroethane, 1,6-hexamethylene diisocyanate, hexamethylphosphonamide, hexane, hydrazine, hydrochloric acid, hydrogen fluoride (hydrofluoric acid), hydrogen sulfide, hydroquinone, isophorone, lindane (all isomers), maleic anhydride, methanol, potassium chloride, methyl bromide (methyl bromide), methyl chloride (methyl chloride), methyl chloroform (1,1,1-trichloroethane), methyl ethyl ketone (2-butanone), methyl hydrazine, methyl iodide (methyl iodide), methyl isobutyl ketone (cyclohexanone), methyl isocyanate, methyl methacrylate, methyl tert-butyl ether, 4,4-methylenebis(2-chloroaniline), methylene chloride, methylene diphenyl diisocyanate (MDI), 4,4'-aminodiphenylmethane, naphthalene, nitrobenzene, 4-Nitrobiphenyl, 4-nitrophenol, 2-nitropropane, N-nitroso-N-methyl urea, N-nitroso dimethylamine, N-nitroso morpholine, Parathion, pentachloronitrobenzene (pentabenzene), pentachlorophenol, phenol, p-phenylenediamine, phosgene, phosphine, phosphorus, phthalic anhydride, polychlorinated biphenyls (Aroclors), 1,3-propane sultone, β-propiolactone, propionaldehyde, propoxur (Baigon), dichloropropane (1,2-dichloropropane), propylene oxide, 1,2-propylene imine (2-methylaziridine), quinoline, quinone, styrene, styrene oxide, 2,3,7,8-tetrachlorodibenzo-p-dioxin, 1,1,2,2-tetrachloroethane, tetrachloroethylene (perchloroethylene), titanium tetrachloride, toluene, 2,4-toluenediamine, 2,4-toluene diisocyanate, o-toluidine, toxaphene (camphene chloride), 1,2,4-trichlorobenzene, 1,1,2-trichloroethane, trichloroethylene, 2,4,5-trichlorophenol, 2,4,6-trichlorophenol, triethylamine, trifluralin, 2,2,4-trimethylpentane, vinyl acetate, bromine ethylene, vinyl chloride, vinylidene chloride (1,1-dichloroethylene), xylene, o-xylene, m-xylene, p-xylene, antimony compounds, arsenic compounds (inorganic, including arsine), beryllium compounds, cadmium compounds, chromium compounds, cobalt compounds, coke oven emissions, cyanide, glycol ethers, lead compounds, manganese compounds, mercury compounds, fine mineral fibers, nickel compounds, polycyclic organic compounds, radioactive nuclides (including radon), selenium compounds, bacteria, fungi, viruses and a combination thereof.

The sensing component 12 of the gas detection module 1 of the present disclosure not only detects the suspended particles in the gas, but also detects the characteristics of the introduced gas. Therefore, the sensing component 12 of the gas detection module 1 further includes a particle sensing element **12*a*, a temperature and humidity sensing element 12*b* and a gas sensing element 12*c*, or is expanded to include other sensing elements, such as a bacteria sensing element 12*d*, a fungus sensing element 12*e* and a virus sensing element 12*f* for detecting the introduced air pollution. Notably, in the embodiment, the sensing component 12 is a particle sensing element 12*a*** for detecting the air pollution data of the suspended particles (PM1, PM2.5, PM10), acetamide, acetonitrile, acetophenone, 2-acetylaminofluorene, acrolein, acrylamide, acrylic acid, acrylonitrile, propylene chloride, 4-aminobiphenyl, aniline, o-anisidine, asbestos, benzidine, biphenyl, di(2-ethylhexyl) phthalate (DEHP), dichloromethyl ether, 1,3-butadiene, calcium cyanamide, caprolactam, captan, carbaryl, catechol, chloramben, chlordane, chloroacetic acid, 2-chloroacetophenone, chlorobenzilate, chloromethyl methyl ether, cresol/methanesulfonic acid (isomers and mixtures), o-cresol, m-cresol, p-cresol, cumene, 2,4-dichlorophenoxyacetic acid, salts and esters, dichlorodiphenyldichloroethylene (DDE), dibenzofuran, dibutyl phthalate, 1,4-dichlorobenzene, 3,3-dichlorobenzidine, dichloroethyl ether (bis(2-chloroethyl)ether), 1,3-dichloropropene, dichlorvos, diethanolamine, N,N-dimethylaniline, diethyl sulfate, 3,3-dimethoxybenzidine, dimethylaminoazobenzene, 3,3'-dimethylbenzidine, dimethylcarbamate chloride, dimethylformamide, 1,1-dimethylhydrazine, dimethyl phthalate, dimethyl sulfate, 4,6-dinitro-o-cresol and its salts, 2,4-dinitrophenol, 2,4-dinitrotoluene, 1,4-dioxane (1,4-ethylene dioxide), 1,2-diphenylhydrazine, epichlorohydrin (1-chloro-2,3-epoxy propane), 1,2-butylene oxide, ethyl acrylate, ethyl urethane (ethyl carbamate), ethylene glycol, ethyleneimine (azirine), ethylene oxide, ethylene thiourea, hexachlorobutadiene, hexachlorocyclopentadiene, 1,6-hexamethylene diisocyanate, hexamethylphosphonamide, hydrazine, hydroquinone, isophorone, lindane (all isomers), maleic anhydride, methyl hydrazine, methyl isobutyl ketone (cyclohexanone), methyl isocyanate, methyl methacrylate, methyl tert-butyl ether, 4,4-methylenebis(2-chloroaniline), methylene diphenyl diisocyanate (MDI), 4,4'-aminodiphenylmethane, naphthalene, nitrobenzene, 4-Nitrobiphenyl, 4-nitrophenol, 2-nitropropane, N-nitroso-N-methyl urea, N-nitroso dimethylamine, N-nitroso morpholine, Parathion, pentachloronitrobenzene (pentabenzene), pentachlorophenol, phenol, p-phenylenediamine, phosphine, phosphorus, phthalic anhydride, polychlorinated biphenyls (Aroclors), 1,3-propane sultone, β-propiolactone, propoxur (Baigon), propylene oxide, 1,2-propylene imine (2-methylaziridine), quinoline, quinone, styrene, styrene oxide, 2,3,7,8-tetrachlorodibenzo-p-dioxin, tetrachloroethylene (perchloroethylene), titanium tetrachloride, 2,4-toluenediamine, 2,4-toluene diisocyanate, o-toluidine, toxaphene (camphene chloride), 2,4,5-trichlorophenol, 2,4,6-trichlorophenol, triethylamine, trifluralin, 2,2,4- trimethylpentane, vinyl acetate, bromine ethylene, vinyl chloride, vinylidene chloride (1,1-dichloroethylene), antimony compounds, arsenic compounds (inorganic, including arsine), beryllium compounds, cadmium compounds, chromium compounds, cobalt compounds, coke oven emissions, cyanide, lead compounds, manganese compounds, mercury compounds, fine mineral fibers, nickel compounds, polycyclic organic compounds, radioactive nuclides or selenium compounds, contained in the gas. Preferably but not exclusively, the sensing component 12 is a temperature and humidity sensing element 12*b* for detecting the air pollution data of the temperature and humidity of the air. Preferably but not exclusively, the sensing component 12 is a gas sensing element 12*c* for detecting the air pollution data of gas molecules contained in the air. The gas molecules can be for example but not limited to ozone, carbon monoxide, carbon dioxide, sulfur dioxide, acetaldehyde, benzene, trichlorotoluene, benzyl chloride, bromoform, 1-bromopropane, carbon disulfide, carbon tetrachloride, carbonyl sulfide, chlorine, chlorobenzene, chloroform, chloroprene diene, diazomethane, 1,2-dibromo-3-chloropropane, ethylbenzene, ethyl chloride, dibromoethane, dichloroethane (1,2-dichloroethane), dichloroethane (1,1-dichloroethane), formaldehyde, heptachlor, hexachlorobenzene, hexachloroethane, hexane, hydrochloric acid, hydrogen fluoride (hydrofluoric acid), hydrogen sulfide, methanol, potassium chloride alcohol, methyl bromide (Methyl bromide), methyl chloride (methyl chloride), methyl chloroform (1,1,1-trichloroethane), methyl ethyl ketone (2-butanone), methyl iodide (methyl iodide), methylene chloride, phosgene, propylene Aldehydes, dichloropropane (1,2-dichloropropane), 1,1,2,2-tetrachloroethane, tetrachloroethylene (perchlorethylene), toluene, 1,2,4-trichlorobenzene, 1,1,2-Trichloroethane, trichloroethylene, xylene, o-xylene, m-xylene, p-xylene, glycol ether, radon and so on. Preferably but not exclusively, the sensing component 12 includes a bacteria sensing element 12*d* for detecting the air pollution data of bacteria contained in the air. Preferably but not exclusively, the sensing component 12 includes a fungus sensing element 12*e* for detecting the air pollution data of fungus contained in the air. Preferably but not exclusively, the sensing component 12 includes a virus sensing element 12*f* for detecting the air pollution data of virus contained in the air. The present disclosure is not limited thereto.

In the embodiment, the particle sensing element 12*a* is disposed in an indoor field A or an outdoor field B and configured to detect if the suspended particulate matter (PM1, PM2.5, PM10) and the concentration of suspended particles contained in the air pollution exceeds a pollution threshold safety value. When the microcontroller 13 receives that the air pollution data of suspend particles exceeds the pollution threshold safety value, a plurality of regulation signals are outputted. Preferably but not exclusively, the pollution threshold safety value of suspended particulate matter 2.5 (PM2.5) includes a concentration of suspended particulate matter 2.5 (PM2.5) less than 15 $\mu g/m^3$. In the embodiment, the temperature and humidity sensing element 12*b* is configured to detect if the temperature and humidity of the air in the indoor field A exceeds a pollution threshold safety value. When the microcontroller 13 receives that the air pollution data of the temperature and humidity of the air exceeds the pollution threshold safety value, a plurality of regulation signals are outputted. Preferably but not exclusively, the pollution threshold safety value of temperature and humidity includes a temperature of 25° C.±3° C. and a humidity of 50%±10%. Preferably but not exclusively, the pollution threshold safety value of temperature and humidity is used to implement a temperature and humidity control in the indoor field A, and the temperature and humidity control is implemented to maintain a temperature of 25° C.±3° C. and a humidity of 50%±10% in the indoor field A. Preferably but not exclusively, the gas sensing element 12*c* is configured to detect if the air pollution data of carbon dioxide ($CO_2$) exceeds a threshold safety value. When the microcontroller 13 receives that the air pollution data of carbon dioxide ($CO_2$) exceeds the pollution threshold safety value, a plurality of regulation signals are outputted. Preferably but not exclusively, the air pollution data of carbon dioxide ($CO_2$) have to be maintained below the pollution threshold safety value of 800 PPM.

Figure 4A:
FIG. 4A is a schematic perspective view illustrating the gas detection module according to the embodiment of the present disclosure.
Figure 4A:
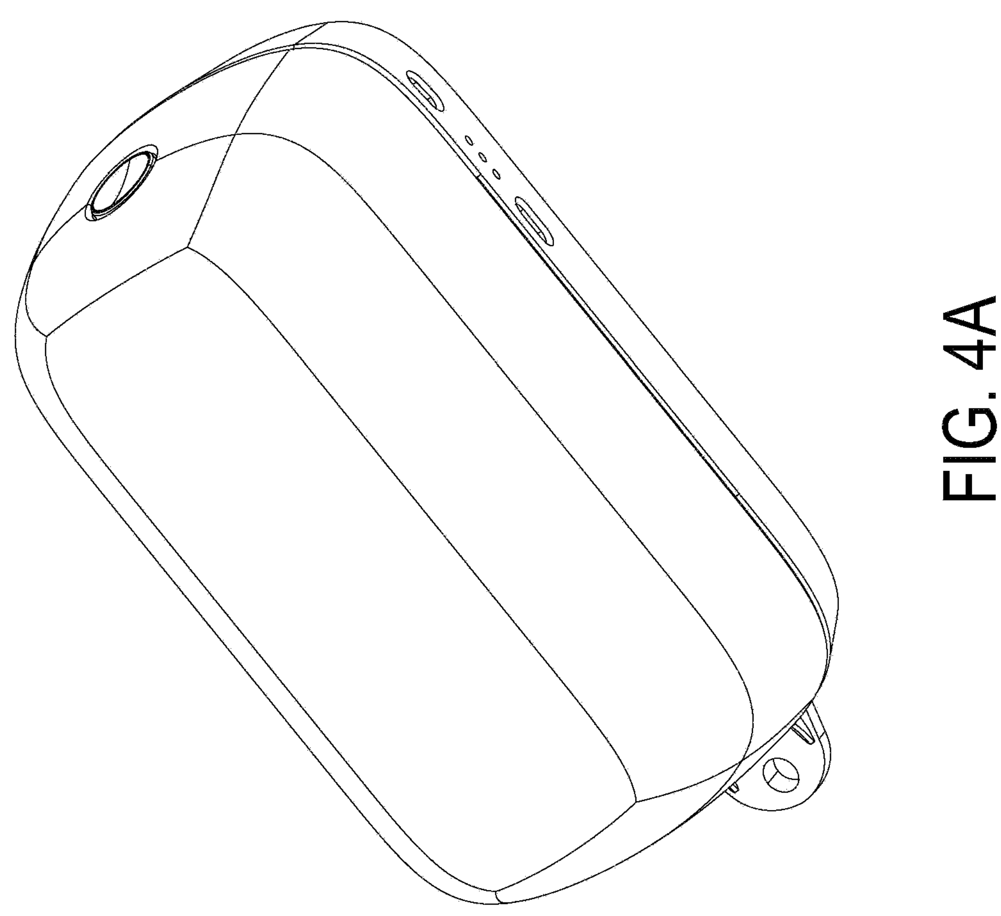
Figure 4B:
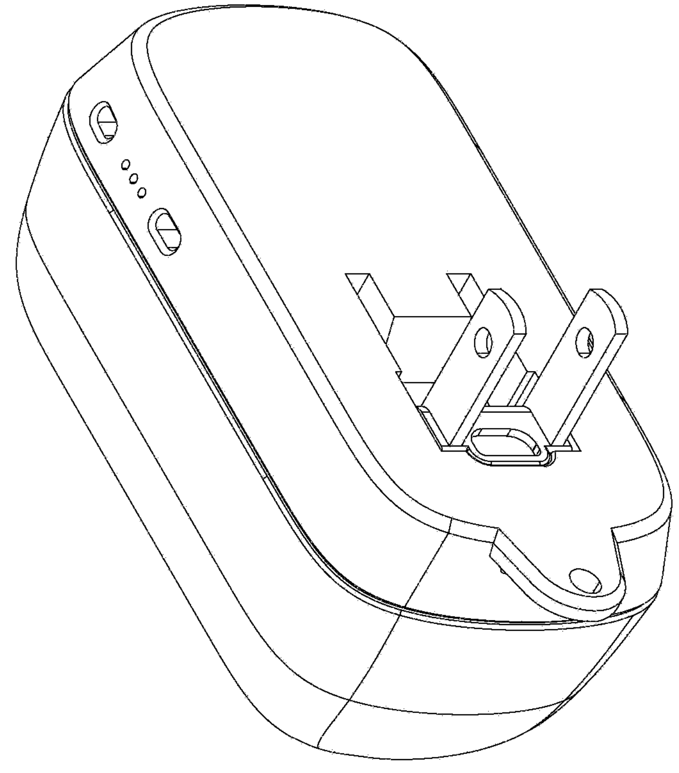
FIG. 4B is a schematic perspective view illustrating the gas detection module implemented in the outdoor field or the indoor field according to the embodiment of the present disclosure and taken from another perspective.
Figure 4B:
Figure 4C:
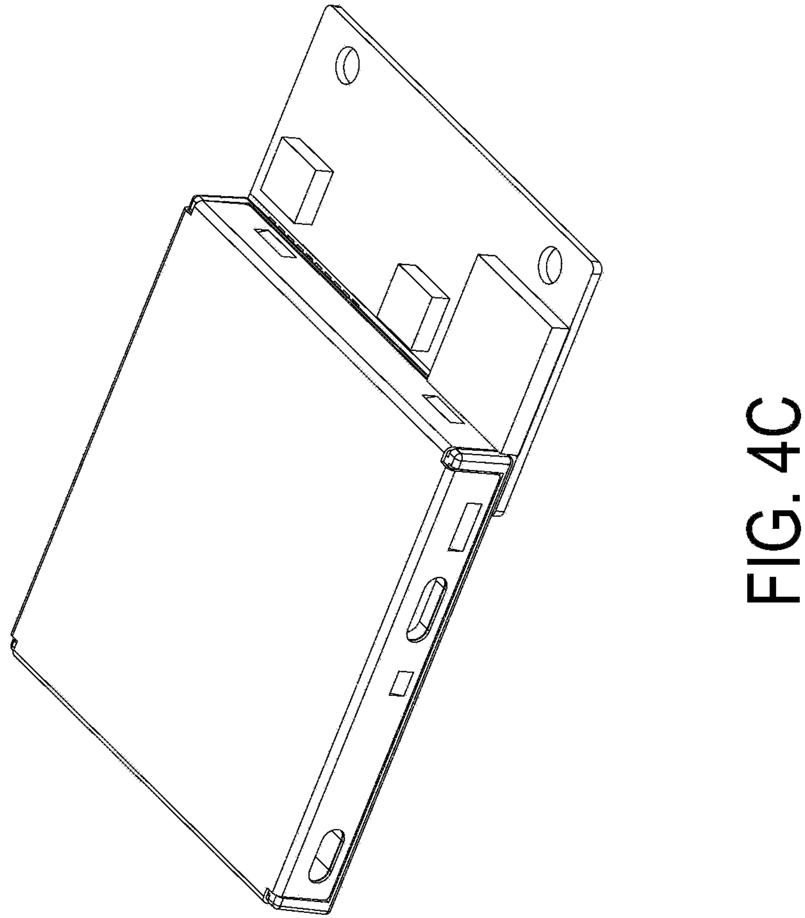
FIG. 4C is a schematic perspective view illustrating the gas detection module according to the embodiment of the present disclosure.

In the embodiment, the microcontroller 13 receives the air pollution data outputted by the sensing component 12, and calculates and processes the air pollution data to outputs the plurality of regulation signals. The air pollution data outputted by the sensing component 12 are transmitted to the microcontroller 13 through a serial communication (IIC) signal for receiving, calculating and processing. The regulation signal outputted by the microcontroller 13 includes a Universal Asynchronous Transceiver and Transceiver (UART) signal and a General Purpose Input and Output (GP I/O) signal. The Universal Asynchronous Transceiver and Transceiver (UART) signals are transmitted through electrical wires to the air cleaning device 2, the wireless communication module 14 and the central control communication interface component 15 for receiving. The General Purpose Input and Output (GP I/O) signals are transmitted through electrical wires to the air cleaning devices 2 for receiving. Notably, as shown in FIG. 2A and FIG. 2B, the central control communication interface component 15 is connected to a communication control line and the central control and regulation device 3 for communication connection and transmission. Preferably but not exclusively, a wired communication transmission (the solid transmission line shown in FIG. 2A) under a RS485 communication protocol is used for communication connection and transmission. Please refer to FIG. 4A and FIG. 4B, again. The gas detection module 1 can be composed of a type including an external power terminal, and the external power terminal is directly inserted into the power interface of the indoor field A or the outdoor field B (e.g., the gas detection module shown in FIG. 1A and FIG. 1B and represented by number 1), so as to start operation of detecting the air pollution. Alternatively, as shown in FIG. 4C, the gas detection module doesn't include an external power terminal, and is directly disposed within the air cleaning device 2 in electrical connection (e.g., the gas detection module shown in FIG. 2A).

Figure 3A:
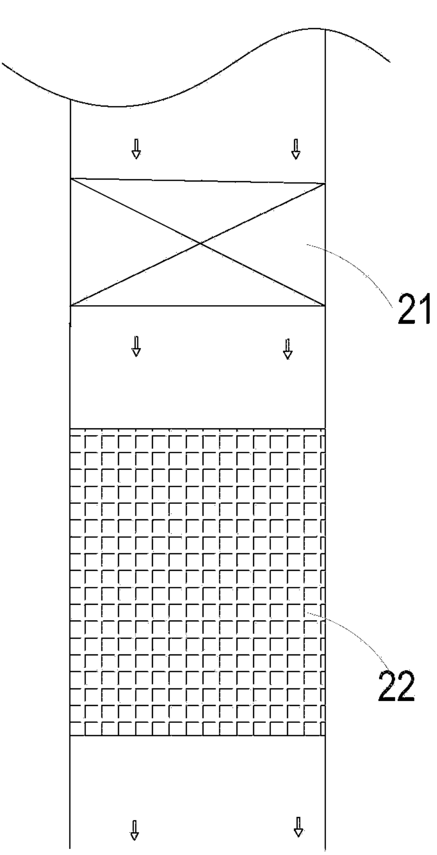
FIG. 3A is a schematic diagram illustrating the combination of the fan and filtering element of the air cleaning device of the present disclosure.
Figure 3B:
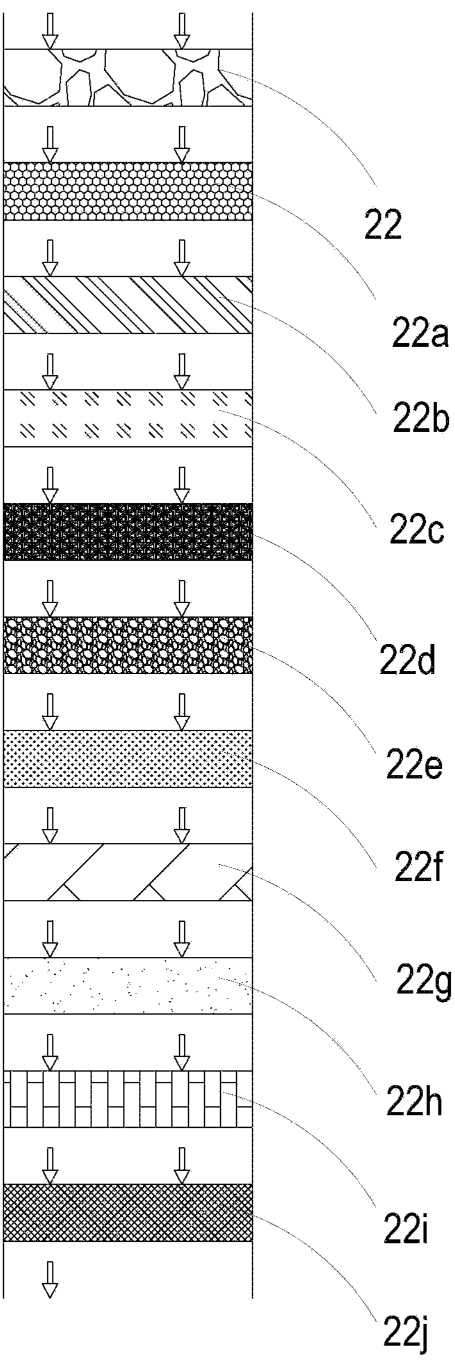
FIG. 3B is a schematic diagram illustrating the combination of the filtering elements of the air cleaning device of the present disclosure.
Figure 3D:
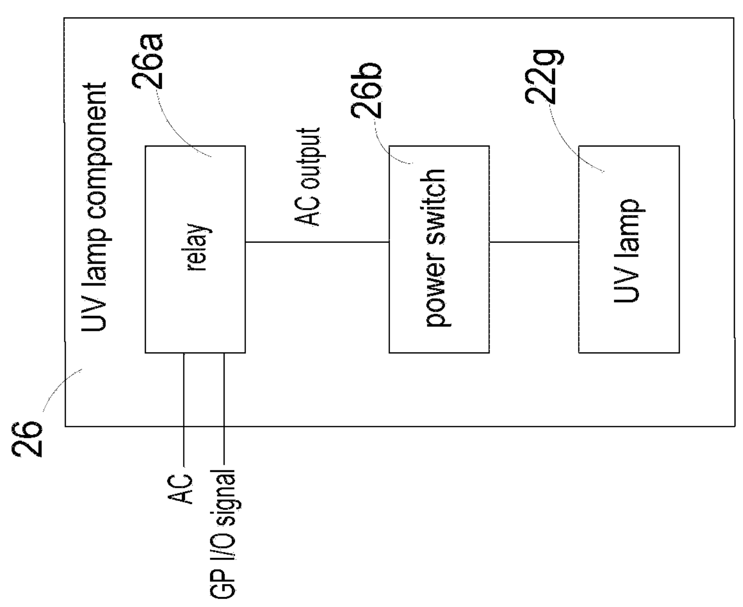
FIG. 3D is a schematic diagram illustrating the regulation operation of the air cleaning device with an ultraviolet lamp component according to an embodiment of the present disclosure.
Figure 3C:
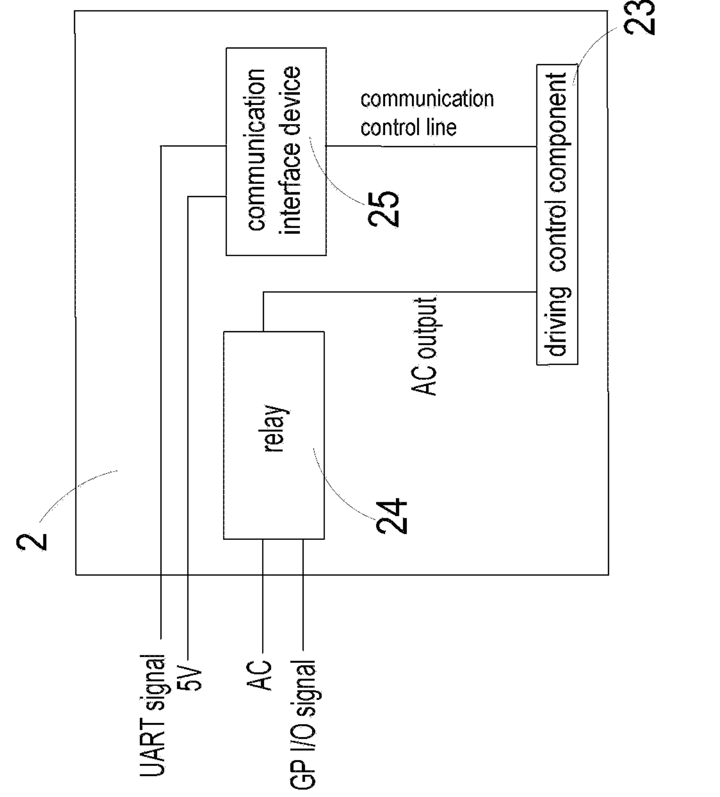
FIG. 3C is a schematic diagram illustrating the regulation operation of relative components of the air cleaning device according to the embodiment of the present disclosure.

Please refer to FIG. 3A and FIG. 3C. In the embodiment, the air cleaning device 2 is disposed in the indoor field A and includes a fan 21, a filtering element 22 and a driving control component 12. Moreover, the gas detection module 1 is disposed within the air cleaning device 2 in electrical connection. The gas detection module 1 can detect the air pollution and output the driving power and the regulation signal. In the embodiment, the gas detection module 1 is electrically connected to the fan 21 and the driving control component 21 (as shown in FIG. 3C). Please further refer to FIG. 2B and FIG. 3C. In the embodiment, the air cleaning device 2 further includes a relay 24 and a communication interface device 25. Preferably but not exclusively, the relay 24 is electrically connected to input the AC voltage outputted by the power conversion component 11 and cooperatively connected to the microcontroller (MCU) 13 to output the regulation signal (i.e., the General Purpose Input and Output (GP I/O) signal), so that the AC voltage is outputted and provided to a driving control component 23 for power control and regulation. Moreover, the communication interface device 25 is connected to input the required DC voltage of 5 V converted by the power conversion component 11, cooperating with the microcontroller (MCU) 13 to input the regulation signal (i.e., the Universal Asynchronous Transceiver and Transceiver (UART) signal) outputted therefrom, and connected to the driving control component 23 for communication connection and transmission through a communication control line to regulate a wind speed of a fan 21 of the air cleaning device 2, so that the fan 21 is controlled to start guiding the air pollution passing through the filtering element 22 for filtration. Notably, in the embodiment, the communication control line of the air cleaning device 2 is used for outputting under a RS485 communication protocol. Notably, in the embodiment, it allows to implement a plurality of air cleaning devices 2 in the present disclosure, each of the air cleaning device includes an address encoder (not shown) for connection with the wire outputting the regulation signal (i.e., the General Purpose Input and Output (GP I/O) signal), so that the plurality of air cleaning devices 2 are serially connected for regulation.

Please refer to FIG. 2B again. In the embodiment, the central control and regulation device 3 is connected with the central control communication interface components 15 of the gas detection modules 1 through the communication control line, provides the control instruction signal under the communication protocol connection to the microcontroller 13 for regulation the operations of the plurality of air cleaning device 2, and receives the air pollution data detected by the gas detection modules 1 for displaying in real time.

Please refer to FIG. 2B and FIG. 3C. In the embodiment, the cloud computing service device 4 receives signals of the air pollution data, which are detected and outputted by the gas detection modules 1 in the plurality of air cleaning devices 2 through wireless communication of a router 5, and stored to form a database of the air pollution data. The cloud computing service device 4 intelligently computes and compares based on the air pollution data, and intelligently selects and issues the control command through wireless communication of the router 5. The control command is transmitted to the gas detection modules 1 in the plurality of air cleaning devices 2 for receiving, and then transmitted to the driving control component 23 to regulate the activation operation of the fan 21. In that, the fan 21 is controlled to start guiding the air pollution passing through the filtering element 22 for filtration, so that the gas state in the indoor field A is cleaned completely to meet the clean room requirement.

Moreover, in the embodiment, the gas detection modules 1 in the plurality of air cleaning devices 2 are connected to the central control and regulation device 3 through the wired communication to receive the signals of the air pollution data, the central control and regulation device 3 transmits the signals of the air pollution data to the router 5 for receiving through wireless communication, and then the signals of the air pollution data are received by the router 5 and transmitted to the cloud computing service device 4, so as to be stored to form the database of the air pollution data. The cloud computing service device 4 intelligently computes and compares based on the air pollution data, the control command is intelligently selected and issued to the central control and regulation device 3 for communication connection, and then the control command is transmitted by the central control and regulation device 3 to the gas detection modules 1 in the plurality of air cleaning devices 2 through wired communication connection for receiving, and then transmitted to the driving control component 23 to regulate the activation operation of the fan 21. The fan 21 is controlled to start guiding the air pollution passing through the filtering element 22 for filtration, so that the gas state in the indoor field A is cleaned completely to meet the clean room requirement.

In the above embodiments, the gas detection modules 1 in the plurality of air cleaning devices 2 are connected to the central control and regulation device 3 under handshake communication protocol of wired communication or wireless communication. When the wireless communication or the wired communication is disconnected, it allows to regulate and select an activation mechanism with the wired communication or the wireless communication that can operate transmission. In that, the cloud computing service device 4 receives the air pollution data through the activation mechanism with the wired communication or the wireless communication that can operate the transmission, intelligently computes and compares based on the air pollution data, and then intelligently selects and issues the control command to be transmitted to the gas detection modules 1 in the plurality of air cleaning devices 2 for receiving under the connection of the activation mechanism with the wired communication or the wireless communication that can operate transmission, and then the control command is transmitted to the driving control component 23 to regulate the activation operation of the fan 21. The fan 21 is controlled to start guiding the air pollution passing through the filtering element 22 for filtration, so that the gas state in the indoor field A is cleaned completely to meet the clean room requirement.

Moreover, the gas detection modules 1 in the plurality of air cleaning devices 2 are connected to the central control and regulation device 3 under the handshake communication protocol of the wired communication or the wireless communication. When the wireless communication and the wired communication are both disconnected, it allows to autonomously compute and compare the air pollution data outputted by the gas detection modules based on the air pollution data, and then transmit the control command to the driving control component 23 to regulate the activation operation of the fan 21. The fan 21 is controlled to start guiding the air pollution passing through the filtering element 22 for filtration, so that the gas state in the indoor field A is cleaned completely to meet the clean room requirement. Notably, in the above embodiments, the intelligently computing includes artificial intelligence (AI) computing or/and edge computing.

From the above, the specific implementation of the indoor air cleaning system in the indoor field A according to the present disclosure can be understood. The specific implementation of the plurality of air cleaning devices 2 in the indoor field A will be described below. The air cleaning device 2 can be installed in the indoor field A through a built-in or plug-in manner. If the air cleaning device 2 is installed in the indoor field A through the built-in manner (as shown in FIG. 1A and FIG. 1B), at least one circulation back-flow channel C is disposed within the indoor field A. The at least one circulation back-flow channel C is surrounded and isolated by several partitions C1 to form on a side of the indoor field A, and includes a plurality of air intakes C2 and a plurality of back-flow vents C3.

Preferably but not exclusively, the air cleaning device 2 is a gas exchanger 2*a*, and the gas exchanger 2*a* is disposed in the circulation back-flow channel C of the indoor field A and corresponding to the air intake C2. Moreover, there is a communication channel (not shown) for implementing ventilation with the outdoor field B. The gas detection module 1 in the gas exchanger 2*a* receives the control command through the wireless communication or the wired communication, and transmits the control command to the driving control component 23 to regulate the activation operation of the fan 21. Furthermore, at least one gas detection module 1 is disposed in the outdoor field B and at least one gas detection module 1 is disposed in the indoor field A for detecting the air pollution. The cloud computing service device 4 receives the air pollution data of the indoor field A and the outdoor field B for storing to form a database of the air pollution data, and intelligently computes and compares the air pollution data of the indoor field A and the outdoor field B. When the air pollution data of the indoor field A is greater than the air pollution data of the outdoor field B, the cloud computing service device 4 issues the control command to be transmitted to the gas detection module 1 in the gas exchanger 2*a* through wireless communication or wired communication for receiving, and then the control command is transmitted to the driving control component 23 to regulate the activation operation of the fan 21, so that it allows to introduce gas from the outdoor field B into the indoor field A for ventilation. Notably, in the embodiment, the air pollution data detected by the gas detection modules 1 of the outdoor field B and the indoor field A are the air pollution data of carbon dioxide ($CO_2$), and the air pollution data of carbon dioxide ($CO_2$) have to be maintained below a pollution threshold safety value of 800 PPM, so that the gas exchanger 2*a* introduces the gas from the outdoor field B into the indoor field A for ventilation when the air pollution data of carbon dioxide ($CO_2$) exceeds the pollution threshold safety value. Notably, in the embodiment, the gas exchanger 2*a* can be example but not limited to a fresh air fan or a complete heat exchanger.

Please refer to FIG. 1A, FIG. 1B and FIG. 3C. Preferably but not exclusively, in the embodiment, the air cleaning device 2 is a circulation filter device 2*b*, and the circulation filter device 2*b* is disposed in the circulation back-flow channel C of the indoor field A and corresponding to the air intake C2. The air pollution is filtered through the filtering element 22, discharged through the air intake C2, and then entering the space of the indoor field A. The gas detection module 1 in the circulation filter device 2*b* transmits the air pollution data externally to the cloud computing service device 4 through wireless communication or wired communication for receiving to form a database of the air pollution data. The cloud computing service device 4 intelligently computes and compares the air pollution data, and intelligently selects and issues the control command to be transmitted to the gas detection module 1 through the wireless communication or the wired communication for receiving, and then the control command is transmitted to the driving control component 23 to regulate the activation operation of the fan 21 of the circulation filter device 2*b*. In that, the air pollution is guided to pass through the filtering element 22 for filtering and entering space of the indoor field A, so that the gas state in the indoor field A is cleaned completely to meet the clean room requirement.

Please refer to FIG. 1B, FIG. 1C and FIG. 3C. Preferably but not exclusively, in the embodiment, the air cleaning device 2 is a negative pressure exhaust fan 2*c*, and the negative pressure exhaust fan 2*c* is disposed in a kitchen unit A1 of the indoor field A. Moreover, the negative pressure exhaust fan 2*c* is disposed in the circulation back-flow channel C of the indoor field A, and has a communication channel (not shown) in communication with the outdoor field B for discharging the air pollution from the indoor field A to the outdoor field B at an accelerated rate. The gas detection module 1 in the negative pressure exhaust fan 2*c* transmits the air pollution data externally to the cloud computing service device 4 through wireless communication or wired communication for receiving to form the database of the air pollution data, and the cloud computing service device 4 intelligently computes and compares the air pollution data, and intelligently selects and issues the control command to be transmitted to the gas detection module 1 through the wireless communication or the wired communication for receiving. Then, the control command is transmitted to the driving control component 23 to regulate the activation operation of the negative pressure exhaust fan 2*c*. In that, the air pollution is guided to pass through the filtering element 22 for filtration, and the air pollution in the indoor field A is discharged to the outdoor field B at an accelerated rate. Notably, in the embodiment, the negative pressure exhaust fan 2*c* is installed in front of the cooking equipment D to directly suck out the air pollution, so that the cook cannot smell the oil smoke, and it prevents the air pollution from spreading to other spaces, such as the living room, but the present disclosure is not limited thereto.

Please refer to FIG. 1B, FIG. 1C and FIG. 3C. Preferably but not exclusively, in the embodiment, the air cleaning device 2 is a hood exchanger 2*d*, and the hood exchanger 2*d* is disposed in a kitchen unit A1 of the indoor field A. Moreover, the hood exchanger 2*d* is disposed in the circulation back-flow channel C of the indoor field A, and has a communication channel (not shown) in communication with the outdoor field B for discharging the air pollution from the indoor field A to the outdoor field B at an accelerated rate. In the embodiment, the gas detection module 1 in the hood exchanger 2*d* transmits the air pollution data externally to the cloud computing service device 4 through wireless communication or wired communication for receiving to form a database of the air pollution data. Moreover, the cloud computing service device 4 intelligently computes and compares the air pollution data, and intelligently selects and issues the control command to be transmitted to the gas detection module 1 through the wireless communication or the wired communication for receiving. Then, the control command is transmitted to the driving control component 23 to regulate the activation operation of the fan 21 of the hood exchanger 2*d*. In that, the air pollution is guided to pass through the filtering element 22 for filtration, and the air pollution in the indoor field A is discharged to the outdoor field B at an accelerated rate.

Please refer to FIG. 1B and FIG. 3C. Preferably but not exclusively, in the embodiment, the air cleaning device 2 is a bathroom exhaust fan 2*e*, and the bathroom exhaust fan 2*e* is disposed in a bathroom unit A2 of the indoor field A. Moreover, the bathroom exhaust fan 2*e* is disposed in the circulation back-flow channel C of the indoor field A, and has a communication channel (not shown) in communication with the outdoor field B for discharging the air pollution from the indoor field A to the outdoor field B at an accelerated rate. The gas detection module 1 in the bathroom exhaust fan 2*e* transmits the air pollution data externally to a cloud computing service device 4 through wireless communication or wired communication for receiving to form a database of the air pollution data. The cloud computing service device 4 intelligently computes and compares the air pollution data, and intelligently selects and issues the control command to be transmitted to the gas detection module 1 through the wireless communication or the wired communication for receiving. Then, the control command is transmitted to the driving control component 23 to regulate the activation operation of the fan 21 of the bathroom exhaust fan 2*e*. In that, the air pollution is guided to pass through the filtering element 22 for filtration, and the air pollution in the indoor field A is discharged to an outdoor field B at an accelerated rate. At same time, the bathroom unit A2 of the indoor field A is allowed to implement a temperature and humidity control. Preferably but not exclusively, the temperature and humidity control is implemented to maintain a temperature of 25° C.±3° C. and a humidity of 50%±10% in the bathroom unit A2 of the indoor field A.

Please refer to FIG. 3A and FIG. 3B. In the above embodiments, the fan 21 of the air cleaning device 2 is controlled and enabled to guide the air pollution to pass through the filtering element 22 for filtration. Preferably but not exclusively, in an embodiment, the filtering element 22 is an ultra low particulate air (ULPA) filter, a high efficiency particulate air (HEPA) filter or a combination thereof, which is configured to absorb the chemical smoke, the bacteria, the dust particles and the pollen contained in the air pollution, so that the air pollution introduced into the filtering element 22 is filtered and purified to achieve the effect of filtering and purification.

In the embodiment, the filtering element 22 of the present disclosure is further combined with physical or chemical materials to provide a sterilization effect on the air pollution, and the airflow of the fan 21 flows in the path indicated by the arrow. As shown in FIG. 3B, in the embodiment, the filtering element 22 includes a decomposition layer coated thereon to sterilize in chemical means. Preferably but not exclusively, the decomposition layer includes an activated carbon 22*a* configured to remove organic and inorganic substances in air pollution, and remove colored and odorous substances. Preferably but not exclusively, the decomposition layer includes a cleansing factor containing chlorine dioxide layer 22*b* configured to inhibit viruses, bacteria, fungi, influenza A, influenza B, enterovirus and norovirus in the air pollution, and the inhibition ratio can reach 99% and more, thereby reducing the cross-infection of viruses. Preferably but not exclusively, the decomposition layer includes an herbal protective layer 22*c* extracted from ginkgo and Japanese *Rhus chinensis* configured to resist allergy effectively and destroy a surface protein of influenza virus (such as H1N1 influenza virus) passing therethrough. Preferably but not exclusively, the decomposition layer includes a silver ion 22*d* configured to inhibit viruses, bacteria and fungi contained in the air pollution. Preferably but not exclusively, the decomposition layer includes a zeolite 22*e* configured to remove ammonia nitrogen, heavy metals, organic pollutants, *Escherichia coli*, phenol, chloroform and anionic surfactants.

Furthermore, in some embodiments, the filtering element 22 is combined with a light irradiation element to sterilize in chemical means. Preferably but not exclusively, the light irradiation element is a photo-catalyst unit including a photo catalyst 22*f* and an ultraviolet lamp 22*g*. When the photo catalyst 22*f* is irradiated by the ultraviolet lamp 22*g*, the light energy is converted into the chemical energy, thereby decomposes harmful gases and disinfects bacteria contained in the air pollution, so as to achieve the effects of filtering and purifying. Preferably but not exclusively, the light irradiation element is a photo-plasma unit including a nanometer irradiation tube 22*h*. When the introduced air pollution is irradiated by the nanometer irradiation tube 22*h*, the oxygen molecules and water molecules contained in the air pollution are decomposed into high oxidizing photo-plasma, and an ion flow capable of destroying organic molecules is generated. In that, volatile formaldehyde, volatile toluene and volatile organic compounds (VOC) contained in the air pollution are decomposed into water and carbon dioxide, so as to achieve the effects of filtering and purifying. Notably, in the embodiment, as shown in FIG. 3D, the air cleaning device 2 further comprises an ultraviolet lamp component 26, the ultraviolet lamp component 26 includes a relay 26*a*, and the relay 26*a* is connected to input an AC voltage outputted from the power conversion component 11 and cooperatively connected to the microcontroller 13 to output the regulation signal( ) so that the AC voltage is outputted and provided to a power switch 26*b*, and the power switch 26*b* is connected to control starting and regulation of the ultraviolet lamp 22*g*. Preferably but not exclusively, the ultraviolet lamp 22*g* is arranged on one side of the filtering element 22 for sterilizing the air pollution.

Moreover, in some embodiments, the filtering element 22 is combined with a decomposition unit to sterilize in chemical means. Preferably but not exclusively, the decomposition unit is a negative ion unit 22*i* with a dust collecting plate. It makes the suspended particles in the air pollution to carry with positive charge and adhered to the dust collecting plate carry with negative charges, so as to achieve the effects of filtering and purifying. Preferably but not exclusively, the decomposition unit is a plasma ion unit 22*j*. The oxygen molecules and water molecules contained in the air pollution are decomposed into positive hydrogen ions ($H^+$) and negative oxygen ions ($O^{2-}$) by the plasma ion. The substances attached with water around the ions are adhered on the surface of viruses and bacteria and converted into OH radicals with extremely strong oxidizing power, thereby removing hydrogen (H) from the protein on the surface of viruses and bacteria, and thus decomposing (oxidizing) the protein, so as to filter the introduced air pollution and achieve the effects of filtering and purifying.

Figure 5:
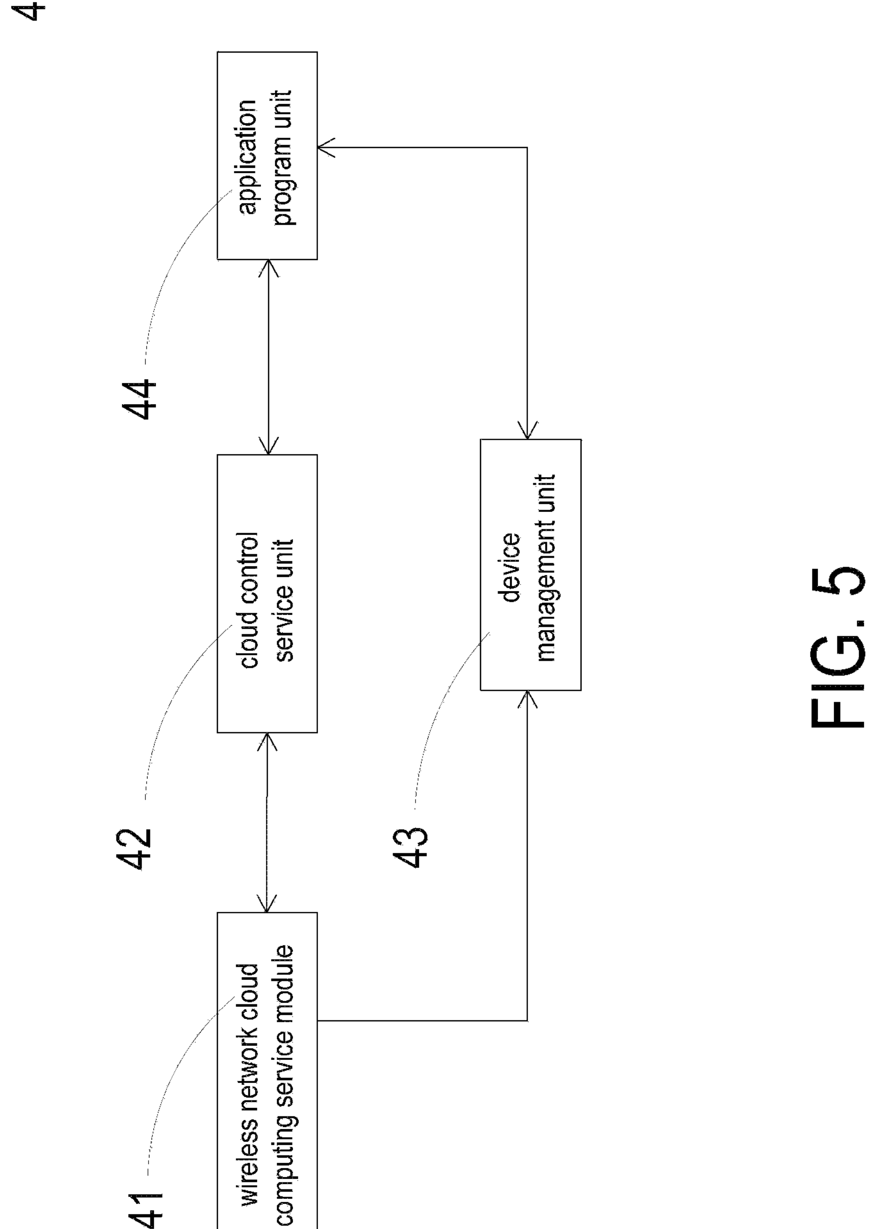
FIG. 5 is a schematic diagram of the architecture of the cloud computing service device according to the embodiment of the present disclosure.

Please refer to FIG. 5. In the above embodiments, the cloud computing service device 4 includes a wireless network cloud computing service module 41, a cloud control service unit 42, a device management unit 43 and an application program unit 44. The wireless network cloud computing service module 41 receives the information of the air pollution data from the gas detection module 1 of the outdoor field B, receives the information of the air pollution data from the gas detection module 1 of the indoor field A, receives the communication information of the air pollution data from the gas detection modules 1 disposed within the plurality of air cleaning devices 2 (such as the gas exchanger 2*a*, the circulation filter device 2*b*, the negative pressure exhaust fan 2*c*, the hood exchanger 2*d* and the bathroom exhaust fan 2*e*) and transmits the control commands. Moreover, the wireless network cloud computing service module 41 receives the information of the air pollution data of the indoor field A and the outdoor field B and transmits the information to the cloud control service unit 42 to store and form a database of the air pollution data. An artificial intelligence calculation is implemented to determine the location of the air pollution through the air pollution database comparison, so that the control command is transmitted to the wireless network cloud computing service module 41, and then transmitted to the devices (such as the air cleaning device 2, the central control and regulation device 3 and the gas exchanger 2*a*) to control the actuation operation through the wireless network cloud computing service module 41. The device management unit 43 receives the communication information of the plurality of air cleaning devices 2 (such as the gas exchanger 2*a*, the circulation filter device 2*b*, the negative pressure exhaust fan 2*c*, the hood exchanger 2*d* and the bathroom exhaust fan 2*e*) through the wireless network cloud computing service module 41 to manage the user login and device binding. The device management information can be provided to the application program unit 44 for system control and management, and the application program unit 44 can also display and inform the air pollution information obtained by the cloud control service unit 42. The user can know the real-time status of air pollution removal through the mobile phone or the communication device. Moreover, the user can control the operation of the indoor air cleaning system through the application program unit 44 of the mobile phone or the communication device.

From the above, the present disclosure provides an indoor air cleaning system. In the specific implementation, the gas detection module 1 is installed on each indoor air cleaning device 2 for detecting the air pollution detection, transmitting the air pollution data, and receiving the control command to electrically connect the driving control component 23 of the air cleaning device 2. The driving control component 23 regulates the activation operation of the fan 21 of the air cleaning device 2, and allows receiving the air pollution data outputted from the gas detection module 1 and transmitted through the wireless communication or the wired communication. Since the communication transmission can be achieved by using the wireless communication or the wired communication, the dual methods of the wired communication and the wireless communication are selected to implement an operable transmission communication mechanism, and a monitoring mechanism is cooperated under the handshake communication protocol of wired communication and wireless communication. An activation mechanism of the wired communication that can operate the transmission or the wireless communication that can operate the transmission is selected through an autonomous judgment for implementing. Thereby, the air pollution data outputted through detecting the air pollution are transmitted to the cloud computing service device 4 through the activation mechanism. Then, the cloud computing service device 4 generates the control command, which is fed back to the gas detection module 1 and transmitted to the driving control component 23 electrically connected. The driving control component 23 regulates the activation operation of the fan 21 of the air cleaning device 2, so that a prevention mechanism of detecting the disconnection of the wireless communication or the wired communication is achieved. In addition, when the gas detection module detects that the wireless communication and the wired communication for outputting the air pollution data are both disconnected, it allows to autonomously compute and compare the air pollution data outputted by the gas detection module 1 based on the air pollution data, and then transmit the control command to the driving control component 23 of the air cleaning device 2 to regulate the activation operation of the fan 21. Consequently, the fan 21 is controlled to start guiding the air pollution passing through the filtering element 22 for filtration, so that the gas state in the indoor field A is cleaned completely to meet the clean room requirement.

Moreover, in the indoor air cleaning system of the present disclosure, the cloud computing service device 4 receives the air pollution data of the indoor field A and the outdoor field B through the wireless communication or the wired communication for storing to form a database of the air pollution data. The intelligent computing comparison based on the database of the air pollution data is performed to intelligently select and output the control command to the fan 21 of the air cleaning device 2 for actuation and regulation operation. Whereby, the fan 21 of the air cleaning device 2 generates an internal circulation directional airflow continuously in the indoor field A, and the air pollution is guided to pass through the filtering element 22 multiple times for filtration. In other words, the cloud computing service device 4 intelligently computes the cleanliness according to the number of suspended particles passing through the indoor field A in real time, intelligently selects and issues the control command to be transmitted to the plurality of the air cleaning devices 2, and timely adjusts and controls the fan 21 of the air cleaning device 2 for actuation, so as to randomly change and adjust the airflow volume and the actuation time period based on the cleanliness of the number of suspended particles in real time. Whereby, the cleaning efficiency of the indoor field A is improved, the environmental noise of the indoor field A is reduced, the internal circulation directional airflow is generated in the indoor field A to generate, and the air pollution is guided to pass through the filtering element 22 multiple times for filtration, so that the gas state in the indoor field A has suspended particles with the particle size less than 2.5 μm to reach a cleanliness of ZAPClean Room 1~9.

As shown in FIG. 6, it defines the classifications of the clean rooms for classifying the gas state in the indoor field A of the present disclosure by counting the suspended particles with the particle size less than 2.5 μm. In the indoor air cleaning system of the present disclosure, the gas state in the indoor field A is allowed to have the suspended particles with the particle size less than 2.5 μm per cubic meter in a number less than 1, so as to reach the cleanliness of ZAPClean Room 1. The gas state in the indoor field A is allowed to have the suspended particles with the particle size less than 2.5 μm per cubic meter in a number less than 10, so as to reach the cleanliness of ZAPClean Room 2. The gas state in the indoor field A is allowed to have the suspended particles with the particle size less than 2.5 μm per cubic foot in a number less than 3 or per cubic meter in a number less than 100, so as to reach the cleanliness of ZAPClean Room 3. The gas state in the indoor field A is allowed to have the suspended particles with the particle size less than 2.5 μm per cubic foot in a number less than 28 or per cubic meter in a number less than 1000, so as to reach the cleanliness of ZAPClean Room 4. The gas state in the indoor field A is allowed to have the suspended particles with the particle size less than 2.5 μm per cubic foot in a number less than 286 or per cubic meter in a number less than 10000, so as to reach the cleanliness of ZAPClean Room 5. The gas state in the indoor field A is allowed to have the suspended particles with the particle size less than 2.5 μm per cubic foot in a number less than 2860 or per cubic meter in a number less than 100000, so as to reach the cleanliness of ZAPClean Room 6. The gas state in the indoor field A is allowed to have the suspended particles with the particle size less than 2.5 μm per cubic foot in a number less than 28600 or per cubic meter in a number less than 1000000, so as to reach the cleanliness of ZAPClean Room 7. The gas state in the indoor field A is allowed to have the suspended particles with the particle size less than 2.5 μm per cubic foot in a number less than 77200 and per cubic meter in a number less than 2720000, so as to reach the cleanliness of ZAPClean Room 8. The gas state in the indoor field A is allowed to have the suspended particles with the particle size less than 2.5 μm per cubic foot in a number less than 154300 or per cubic meter in a number less than 5440000, so as to reach the cleanliness of ZAPClean Room 9.

In summary, the present disclosure provides an indoor air cleaning system including a plurality of gas detection modules, a plurality of air cleaning devices and at least one central control and regulation device. Each air cleaning device is combined and electrically connected with a gas detection module disposed thereon for implementing air pollution detection and coordinating the regulation operations. Moreover, the central control and regulation device is connected with the gas detection module, and able to select an activation mechanism under the handshake communication protocol of wired communication or wireless communication for transmitting and connecting, so that control instruction signals are provided for the gas detection modules regulating the activation operations, the air volume and the noise of the plurality of air cleaning devices. It allows the air pollution to pass through the filtering elements of the air cleaning devices for filtration, so that the gas state in the indoor field is cleaned completely to meet the clean room requirements for safe breathing. It avoids being exposed to hazardous gas in the environment that may cause the human health impacts and injuries. The present disclosure includes the industrial applicability and the inventive steps.

What is claimed is:

1. An indoor air cleaning system, comprising:

a plurality of gas detection modules for detecting air pollution and outputting air pollution data, which are calculated and processed to output a plurality of regulation signals;

a plurality of air cleaning devices disposed in an indoor field, and each comprising a fan, a filtering element and a driving control component, wherein the plurality of gas detection modules are disposed within the plurality of air cleaning devices, and electrically connected to the fan and the driving control component, wherein the driving control component regulates an activation operation, airflow volume and noise of the fan according to the plurality of regulation signals received, and the fan is controlled to start guiding the air pollution passing through the filtering element for filtration; and at least one central control and regulation device connected with central control communication interface components of the plurality of gas detection modules, wherein the at least one central control and regulation device is connected under handshake communication protocol of wired communication or wireless communication to provide a control instruction signal to the gas detection module for regulating operations of the fans of the plurality of air cleaning devices, and receives the air pollution data detected by the gas detection modules for displaying in real time;

wherein the plurality of gas detection modules receive a control command and transmit the control command to the driving control components to regulate the activation operations of fans, whereby the fan is controlled to start guiding the air pollution passing through the filtering element for filtration, thereby the gas state in the indoor field is cleaned completely to meet a clean room requirement, wherein the indoor air cleaning system further comprises a cloud computing service device, wherein the cloud computing service device receives signals of the air pollution data, which are detected and outputted by the gas detection modules in the plurality of air cleaning devices through wireless communication of a router, and stored to form a database of the air pollution data, wherein the cloud computing service device intelligently computes and compares based on the air pollution data, and the intelligently computing includes artificial intelligence (AI) computing or/and edge computing, wherein the control command is intelligently selected and issued through wireless communication of the router, transmitted to the gas detection modules in the plurality of air cleaning devices for receiving, then transmitted to the driving control component to regulate the activation operation of the fan, wherein the fan is controlled to start guiding the air pollution passing through the filtering element for filtration, therefore the gas state in the indoor field is cleaned completely to meet the clean room requirement.

2. The indoor air cleaning system according to claim 1, wherein the air pollution is at least one selected from the group consisting of particulate matter, ozone, carbon monoxide, carbon dioxide, sulfur dioxide, nitrogen dioxide, acetaldehyde, acetamide, acetonitrile, acetophenone, 2-acetylaminofluorene, acrolein, acrylamide, acrylic acid, acrylonitrile, propylene chloride, 4-aminobiphenyl, aniline, o-anisidine, asbestos, benzene, benzidine, trichlorotoluene, benzyl chloride, biphenyl, di(2-ethylhexyl) phthalate (DEHP), dichloromethyl ether, tribromoform, 1-bromopropane, 1,3-butadiene, calcium cyanamide, caprolactam, captan, carbaryl, carbon disulfide, carbon tetrachloride, carbonyl sulfide, catechol, chloramben, chlordane, chlorine, chloroacetic acid, 2-chloroacetophenone, chlorobenzene, chlorobenzilate, chloroform, chloromethyl methyl ether, chloroprene, cresol/methanesulfonic acid (isomers and mixtures), o-cresol, m-cresol, p-cresol, cumene, 2,4-dichlorophenoxyacetic acid, salts and esters, dichlorodiphenyldichloroethylene (DDE), diazomethane, dibenzofuran, 1,2-dibromo-3-chloropropane, dibutyl phthalate, 1,4-dichlorobenzene, 3,3-dichlorobenzidine, dichloroethyl ether (bis(2-chloroethyl) ether), 1,3-dichloropropene, dichlorvos, diethanolamine, N,N-dimethylaniline, diethyl sulfate, 3,3-dimethoxybenzidine, dimethylaminoazobenzene, 3,3'-dimethylbenzidine, dimethylcarbamate chloride, dimethylformamide, 1,1-dimethylhydrazine, dimethyl phthalate, dimethyl sulfate, 4,6-dinitro-o-cresol and its salts, 2,4-dinitrophenol, 2,4-dinitrotoluene, 1,4-dioxane (1,4-ethylene dioxide), 1,2-diphenylhydrazine, epichlorohydrin (1-chloro-2,3-epoxy propane), 1,2-butylene oxide, ethyl acrylate, ethylbenzene, ethyl urethane (ethyl carbamate), ethyl chloride, dibromoethane, dichloroethane (1,2-dichloro ethane), ethylene glycol, ethyleneimine (azirine), ethylene oxide, ethylene thiourea, dichloroethane (1,1-dichloroethane), formaldehyde, heptachlor, hexachlorobenzene, hexachlorobutadiene, hexachlorocyclopentadiene, hexachloroethane, 1,6-hexamethylene diisocyanate, hexamethylphosphonamide, hexane, hydrazine, hydrochloric acid, hydrogen fluoride (hydrofluoric acid), hydrogen sulfide, hydroquinone, isophorone, lindane (all isomers), maleic anhydride, methanol, methoxychlor, methyl bromide (methyl bromide), methyl chloride (methyl chloride), methyl chloroform (1,1,1-trichloroethane), methyl ethyl ketone (2-butanone), methyl hydrazine, methyl iodide (methyl iodide), methyl isobutyl ketone (cyclohexanone), methyl isocyanate, methyl methacrylate, methyl tert-butyl ether, 4,4-methylenebis(2-chloroaniline), methylene chloride, methylene diphenyl diisocyanate (MDI), 4,4'-aminodiphenylmethane, naphthalene, nitrobenzene, 4-Nitrobiphenyl, 4-nitrophenol, 2-nitropropane, N-nitroso-N-methyl urea, N-nitroso dimethylamine, N-nitroso morpholine, Parathion, pentachloronitrobenzene (pentabenzene), pentachlorophenol, phenol, p-phenylenediamine, phosgene, phosphine, phosphorus, phthalic anhydride, polychlorinated biphenyls (Aroclors), 1,3-propane sultone, β-propiolactone, propionaldehyde, propoxur (Baigon), dichloropropane (1,2-dichloropropane), propylene oxide, 1,2-propylene imine (2-methylaziridine), quinoline, quinone, styrene, styrene oxide, 2,3,7,8-tetrachlorodibenzo-p-dioxin, 1,1,2,2-tetrachloroethane, tetrachloroethylene (perchloroethylene), titanium tetrachloride, toluene, 2,4-toluenediamine, 2,4-toluene diisocyanate, o-toluidine, toxaphene (camphene chloride), 1,2,4-trichlorobenzene, 1,1,2-trichloroethane, trichloroethylene, 2,4,5-trichlorophenol, 2,4,6-trichlorophenol, triethylamine, trifluralin, 2,2,4-trimethylpentane, vinyl acetate, bromine ethylene, vinyl chloride, vinylidene chloride (1,1-dichloroethylene), xylene, o-xylene, m-xylene, p-xylene, antimony compounds, arsenic compounds (inorganic, including arsine), beryllium compounds, cadmium compounds, chromium compounds, cobalt compounds, coke oven emissions, cyanide, glycol ethers, lead compounds, manganese compounds, mercury compounds, fine mineral fibers, nickel compounds, polycyclic organic compounds, radioactive nuclides (including radon), selenium compounds, bacteria, fungi, and viruses.

3. The indoor air cleaning system according to claim 1, wherein the gas detection module comprises at least one power conversion component, at least one sensing component, at least one microcontroller, at least one wireless communication component and at least one central control communication interface component, wherein the power conversion component provides required power to the sensing component, the microcontroller, the wireless communication component and the central control communication interface component, the sensing component detects the air pollution and outputs the air pollution data for the microcontroller calculating and processing, the microcontroller outputs the plurality of regulation signals, and the sensing component comprises a sensing element detecting the air pollution.

4. The indoor air cleaning system according to claim 3, wherein the sensing element is one selected from the group consisting of a particle sensing element, a temperature and humidity sensing element, and a gas sensing element for detecting the air pollution data of suspended particles contained in air, the air pollution data of temperature and humidity, and the air pollution data of gas molecules contained in air respectively.

5. The indoor air cleaning system according to claim 3, wherein the sensing element is one selected from the group consisting of a bacteria sensing element, a fungus sensing element, and a virus sensing element for detecting the air pollution data of bacteria contained in air, air pollution data of fungus contained in air, and air pollution data of virus contained in air respectively.

6. The indoor air cleaning system according to claim 1, wherein the gas detection modules in the plurality of air cleaning devices are connected to the central control and regulation device to receive the signals of the air pollution data, the central control and regulation device transmits the signals of the air pollution data to the router for receiving through wireless communication, and then the signals of the air pollution data are received by the router and transmitted to the cloud computing service device, so as to be stored to form the database of the air pollution data, wherein the cloud computing service device intelligently computes and compares based on the air pollution data, the control command is intelligently selected and issued to the central control and regulation device for communication connection, and then the control command is transmitted by the central control and regulation device to the gas detection modules in the plurality of air cleaning devices through wired communication connection for receiving, and then transmitted to the driving control component to regulate the activation operation of the fan, wherein the fan is controlled to start guiding the air pollution passing through the filtering element for filtration, so that the gas state in the indoor field is cleaned completely to meet the clean room requirement.

7. The indoor air cleaning system according to claim 1, wherein the gas detection modules in the plurality of air cleaning devices are connected to the central control and regulation device under handshake communication protocol of wired communication or wireless communication, wherein when the wireless communication or the wired communication is disconnected, it allows to regulate and select an activation mechanism with the wired communication or the wireless communication that can operate transmission, wherein the cloud computing service device receives the air pollution data through the activation mechanism with the wired communication or the wireless communication that can operate the transmission, intelligently computes and compares based on the air pollution data, and then intelligently selects and issues the control command to be transmitted to the gas detection modules in the plurality of air cleaning devices for receiving under the connection of the activation mechanism with the wired communication or the wireless communication that can operate transmission, and then the control command is transmitted to the driving control component to regulate the activation operation of the fan, wherein the fan is controlled to start guiding the air pollution passing through the filtering element for filtration, so that the gas state in the indoor field is cleaned completely to meet the clean room requirement.

8. The indoor air cleaning system according to claim 7, wherein the gas detection modules in the plurality of air cleaning devices are connected to the central control and regulation device under the handshake communication protocol of the wired communication or the wireless communication, wherein when the wireless communication and the wired communication are both disconnected, it allows to autonomously compute and compare the air pollution data outputted by the gas detection modules based on the air pollution data, and then transmit the control command to the driving control component to regulate the activation operation of the fan, wherein the fan is controlled to start guiding the air pollution passing through the filtering element for filtration, so that the gas state in the indoor field is cleaned completely to meet the clean room requirement.

9. The indoor air cleaning system according to claim 1, further comprising at least one gas detection module disposed in an outdoor field and at least one gas detection module disposed in the indoor field for detecting the air pollution in the outdoor field and the indoor field, wherein the cloud computing service device receives the air pollution data of the indoor field and the outdoor field for storing to form a database of the air pollution data, and intelligently computes and compares the air pollution data of the indoor field and the outdoor field, wherein when the air pollution data of the indoor field is greater than the air pollution data of the outdoor field, the cloud computing service device issues the control command to be transmitted to the air cleaning device through wireless communication or wired communication, and the air cleaning device is a gas exchanger, wherein the gas detection module in the gas exchanger receives the control command through the wireless communication or the wired communication and transmits the control command to the driving control component to regulate the activation operation of the fan, so that it allows to introduce gas from the outdoor field into the indoor field for ventilation.

10. The indoor air cleaning system according to claim 9, wherein the air pollution data detected by the gas detection modules of the outdoor field and the indoor field are the air pollution data of carbon dioxide ($CO_2$), and the air pollution data of carbon dioxide ($CO_2$) have to be maintained below a pollution threshold safety value of 800 PPM,wherein the gas exchanger introduces the gas from the outdoor field into the indoor field for ventilation when the air pollution data of carbon dioxide ($CO_2$) exceeds the pollution threshold safety value.

11. The indoor air cleaning system according to claim 9, wherein the gas exchanger is a fresh air fan, a complete heat exchanger or a combination thereof.

12. The indoor air cleaning system according to claim 1, wherein the air cleaning device is a circulation filter device, wherein the gas detection module in the circulation filter device transmits the air pollution data externally to the cloud computing service device through wireless communication or wired communication to form a database of the air pollution data, and the cloud computing service device intelligently computes and compares the air pollution data, and intelligently selects and issues the control command to be transmitted to the gas detection module through the wireless communication or the wired communication for receiving, and then the control command is transmitted to the driving control component to regulate the activation operation of the fan of the circulation filter device, wherein the air pollution is guided to pass through the filtering element for filtering and entering space of the indoor field, so that the gas state in the indoor field is cleaned completely to meet the clean room requirement.

13. The indoor air cleaning system according to claim 1, wherein the air cleaning device is a negative pressure exhaust fan, which is disposed in a kitchen unit of the indoor field, wherein the gas detection module in the negative pressure exhaust fan transmits the air pollution data externally to the cloud computing service device through wireless communication or wired communication to form the database of the air pollution data, and the cloud computing service device intelligently computes and compares the air pollution data, and intelligently selects and issues the control command to be transmitted to the gas detection module through the wireless communication or the wired communication for receiving, and then the control command is transmitted to the driving control component to regulate the activation operation of the negative pressure exhaust fan, wherein the air pollution is guided to pass through the filtering element for filtration, and the air pollution in the indoor field is discharged to an outdoor field at an accelerated rate.

14. The indoor air cleaning system according to claim 1, wherein the air cleaning device is a hood exchanger, which is disposed in a kitchen unit of the indoor field, wherein the gas detection module in the hood exchanger transmits the air pollution data externally to the cloud computing service device through wireless communication or wired communication to form a database of the air pollution data, and the cloud computing service device intelligently computes and compares the air pollution data, and intelligently selects and issues the control command to be transmitted to the gas detection module through the wireless communication or the wired communication for receiving, and then the control command is transmitted to the driving control component to regulate the activation operation of the fan of the hood exchanger, wherein the air pollution is guided to pass through the filtering element for filtration, and the air pollution in the indoor field is discharged to an outdoor field at an accelerated rate.

15. The indoor air cleaning system according to claim 1, wherein the air cleaning device is a bathroom exhaust fan, which is disposed in a bathroom unit of the indoor field, wherein the gas detection module in the bathroom exhaust fan transmits the air pollution data externally to the cloud computing service device through wireless communication or wired communication to form a database of the air pollution data, and the cloud computing service device intelligently computes and compares the air pollution data, and intelligently selects and issues the control command to be transmitted to the gas detection module through the wireless communication or the wired communication for receiving, and then the control command is transmitted to the driving control component to regulate the activation operation of the bathroom exhaust fan, wherein the air pollution is guided to pass through the filtering element for filtration, and the air pollution in the indoor field is discharged to an outdoor field at an accelerated rate, wherein the bathroom unit of the indoor field is allowed to implement a temperature and humidity control, and the temperature and humidity control is implemented to maintain a temperature of 25° C.±3° C. and a humidity of 50%±10% in the indoor field.

16. The indoor air cleaning system according to claim 3, wherein the air cleaning device further comprises a relay and a communication interface device, wherein the relay is electrically connected to input an AC voltage outputted by the power conversion component and cooperatively connected to the microcontroller to output the regulation signal, so that the AC voltage is outputted and provided to the driving control component for power control and regulation, wherein the communication interface device is connected to input a required DC voltage outputted by the power conversion component, cooperatively connected to the microcontroller to output the regulation signal, and connected to the driving control component for communication connection and transmission through a communication control line to regulate a wind speed of the fan of the air cleaning device.

17. The indoor air cleaning system according to claim 1, wherein the filtering element is an ultra low particulate air (ULPA) filter, a high efficiency particulate air (HEPA) filter or a combination thereof.

18. The indoor air cleaning system according to claim 3, wherein the air cleaning device further comprises an ultraviolet lamp component, the ultraviolet lamp component comprises a relay, and the relay is connected to input an AC voltage outputted from the power conversion component and cooperatively connected to the microcontroller to output the regulation signal, so that the AC voltage is outputted and provided to a power switch, and the power switch is connected to control starting and regulation of an ultraviolet lamp, wherein the ultraviolet lamp is arranged on one side of the filtering element for sterilizing the air pollution.

19. The indoor air cleaning system according to claim 1, wherein the cloud computing service device comprises a wireless network cloud computing service module, a cloud control service unit, a device management unit and an application program unit, wherein the cloud computing service device intelligently computes a cleanliness according to a number of suspended particles passing through the indoor field in real time, and intelligently selects and issues the control command to be transmitted to the gas detection modules in the plurality of air cleaning devices for receiving, and then the control command is transmitted to the driving control component to timely regulate the activation operation of the fan of the air cleaning device, so as to randomly change and adjust the airflow volume and the actuation time period based on the cleanliness of the number of suspended particles in real time, whereby the cleaning efficiency of the indoor field is improved, the environmental noise of the indoor field is reduced, an internal circulation directional airflow is generated in the indoor field, and the air pollution is guided to pass through the filtering element multiple times for filtration, so that the gas state in the indoor field is cleaned completely to meet a clean room requirement.

* * * * *